US012779186B2

(12) United States Patent
Christopher et al.

(10) Patent No.: US 12,779,186 B2
(45) Date of Patent: Nov. 3, 2026

(54) CEREBRAL SPINAL FLUID SHUNT PLUG

(71) Applicant: Longeviti Neuro Solutions, Inc., Hunt Valley, MD (US)

(72) Inventors: Jesse Christopher, Hunt Valley, MD (US); Bradley Rabinovitz, Severna Park, MD (US); Todd Johnson, Chalfont, PA (US)

(73) Assignee: LONGEVITI NEURO SOLUTIONS, INC., Baltimore, MD (US)

( * ) Notice: Subject to any disclaimer, the term of this patent is extended or adjusted under 35 U.S.C. 154(b) by 1109 days.

(21) Appl. No.: 17/821,353

(22) Filed: Aug. 22, 2022

(65) Prior Publication Data

US 2022/0395676 A1 Dec. 15, 2022

Related U.S. Application Data

(63) Continuation of application No. 17/450,878, filed on Oct. 14, 2021, now Pat. No. 12,569,655, which is a continuation-in-part of application No. 16/662,624, filed on Oct. 24, 2019, now Pat. No. 11,439,798, which is a continuation-in-part of application No.
(Continued)

(51) Int. Cl.
*A61M 27/00* (2006.01)
*A61L 29/06* (2006.01)

(52) U.S. Cl.
CPC ............ *A61M 27/006* (2013.01); *A61L 29/06* (2013.01); *A61M 2205/04* (2013.01); *A61M 2205/3303* (2013.01); *A61M 2205/3523* (2013.01)

(58) Field of Classification Search
CPC ............ A61M 27/006; A61M 2250/04; A61M 2250/3303; A61M 2250/3523; A61B 5/031; A61B 5/0004; A61N 1/0539
See application file for complete search history.

(56) References Cited

U.S. PATENT DOCUMENTS

| | | | |
|---|---|---|---|
| 3,111,125 A | 11/1963 | Schulte | |
| 3,310,051 A | 3/1967 | Schulte | |

(Continued)

FOREIGN PATENT DOCUMENTS

| | | | |
|---|---|---|---|
| CA | 219104 A | 5/1922 | |
| CA | 2154700 A1 | 6/1994 | |

(Continued)

*Primary Examiner* — Philip R Wiest
(74) *Attorney, Agent, or Firm* — Welsh Flaxman & Gitler LLC

(57) ABSTRACT

A cerebral spinal fluid shunt plug includes a shunt plug housing having a shunt valve recess formed therein and a window recess with an access hole. The cerebral spinal fluid shunt plug also includes a shunt valve shaped and dimensioned for positioning within the shunt valve recess of the shunt plug housing and a lucent disk shaped and dimensioned for the passage through the central access hole of the shunt plug housing. In another embodiment, a cerebral spinal fluid shunt plug includes a shunt plug housing having a shunt valve recess formed therein and an intracranial monitoring device recess with an access hole. A shunt valve is positioned within the shunt valve recess of the shunt plug housing and an intracranial monitoring device is passed through the central access hole of the shunt plug housing.

10 Claims, 32 Drawing Sheets

Related U.S. Application Data

15/830,529, filed on Dec. 4, 2017, now Pat. No. 11,045,632.

(60) Provisional application No. 63/092,606, filed on Oct. 16, 2020, provisional application No. 62/488,966, filed on Apr. 24, 2017.

(56) References Cited

U.S. PATENT DOCUMENTS

| | | | | |
|---|---|---|---|---|
| 3,827,439 | A | 8/1974 | Schulte et al. | |
| 3,889,687 | A | 6/1975 | Harris et al. | |
| 3,985,140 | A * | 10/1976 | Harris | A61M 27/006 604/9 |
| 4,206,762 | A | 6/1980 | Cosman | |
| 4,281,667 | A | 8/1981 | Cosman | |
| 4,390,018 | A | 6/1983 | Zukowski | |
| 4,475,898 | A | 10/1984 | Brodner et al. | |
| 4,551,128 | A | 11/1985 | Hakim et al. | |
| 4,660,568 | A | 4/1987 | Cosman | |
| 4,781,673 | A | 11/1988 | Watanabe | |
| 4,885,002 | A | 12/1989 | Watanabe et al. | |
| 4,950,232 | A | 8/1990 | Ruzicka et al. | |
| 5,360,407 | A | 11/1994 | Leonard | |
| 5,458,606 | A | 10/1995 | Cohen et al. | |
| 5,464,446 | A | 11/1995 | Dreessen et al. | |
| 5,634,894 | A * | 6/1997 | Magram | A61M 27/006 604/9 |
| 5,643,195 | A | 7/1997 | Drevet et al. | |
| 5,928,182 | A * | 7/1999 | Kraus | A61M 27/006 604/9 |
| 6,146,352 | A | 11/2000 | Bonnal | |
| 6,152,933 | A * | 11/2000 | Werp | A61M 27/006 604/165.01 |
| 6,348,042 | B1 | 2/2002 | Warren, Jr. | |
| 6,383,159 | B1 | 5/2002 | Saul et al. | |
| 6,533,733 | B1 * | 3/2003 | Ericson | A61M 27/006 600/128 |
| 6,875,192 | B1 | 4/2005 | Saul et al. | |
| 7,212,864 | B2 | 5/2007 | Wahlstrand et al. | |
| 7,235,060 | B2 * | 6/2007 | Kraus | A61M 27/006 604/9 |
| 7,242,982 | B2 | 7/2007 | Singhal et al. | |
| 7,346,391 | B1 | 3/2008 | Osorio et al. | |
| 7,582,068 | B2 | 9/2009 | Koullick et al. | |
| 7,596,408 | B2 | 9/2009 | Singhal et al. | |
| 7,976,517 | B2 | 7/2011 | Dextradeur et al. | |
| 8,038,685 | B2 * | 10/2011 | Bedenbaugh | A61N 1/0539 607/116 |
| 8,202,090 | B2 | 6/2012 | Shachar | |
| 8,221,392 | B2 | 7/2012 | Dextradeur et al. | |
| 8,480,612 | B2 * | 7/2013 | Kassem | A61B 5/031 604/9 |
| 8,504,163 | B1 | 8/2013 | Meadows | |
| 8,940,799 | B2 | 1/2015 | Bertrand et al. | |
| 9,101,756 | B1 | 8/2015 | Pianca et al. | |
| 9,457,180 | B2 | 10/2016 | Bucholz | |
| 9,592,377 | B2 | 3/2017 | Greenberg et al. | |
| 9,675,783 | B2 | 6/2017 | Asaad et al. | |
| 9,713,429 | B2 | 7/2017 | Schmidt et al. | |
| 9,861,799 | B2 | 1/2018 | Trescony et al. | |
| 10,215,597 | B2 * | 2/2019 | Gagne | G01D 11/30 |
| 10,639,461 | B2 * | 5/2020 | Anand | A61M 27/006 |
| 10,792,480 | B2 * | 10/2020 | Anand | A61M 25/0075 |
| 11,045,632 | B2 * | 6/2021 | Christopher | A61M 27/006 |
| 2003/0199831 | A1 | 10/2003 | Morris et al. | |
| 2004/0220510 | A1 | 11/2004 | Koullick et al. | |
| 2005/0059922 | A1 | 3/2005 | Kuhlman et al. | |
| 2005/0143799 | A1 * | 6/2005 | Black | A61B 5/6864 607/116 |
| 2006/0020239 | A1 * | 1/2006 | Geiger | A61B 5/076 604/9 |
| 2006/0173522 | A1 * | 8/2006 | Osorio | A61N 1/0553 607/116 |
| 2006/0211946 | A1 * | 9/2006 | Mauge | A61F 2/2476 600/488 |
| 2007/0198026 | A1 * | 8/2007 | Cauthen | A61M 25/04 606/108 |
| 2008/0262406 | A1 | 10/2008 | Wiener | |
| 2009/0112277 | A1 | 4/2009 | Wingeier et al. | |
| 2009/0112308 | A1 * | 4/2009 | Kassem | A61M 39/22 340/505 |
| 2009/0112327 | A1 | 4/2009 | Ane et al. | |
| 2010/0076366 | A1 | 3/2010 | Henderson, Sr. et al. | |
| 2011/0066072 | A1 | 3/2011 | Kawoos et al. | |
| 2012/0046595 | A1 * | 2/2012 | Wilson | F16K 31/088 604/9 |
| 2013/0085441 | A1 * | 4/2013 | Aihara | A61M 5/14276 604/9 |
| 2014/0073859 | A1 * | 3/2014 | Schorn | A61N 1/0539 600/300 |
| 2014/0074202 | A1 | 3/2014 | Bedenbaugh | |
| 2014/0336560 | A1 | 11/2014 | Hakim | |
| 2014/0350635 | A1 * | 11/2014 | Strother | A61N 1/37518 607/45 |
| 2015/0005800 | A1 | 1/2015 | Anile | |
| 2016/0263361 | A1 * | 9/2016 | Vadivelu | A61M 25/02 |
| 2017/0156596 | A1 * | 6/2017 | Aguilar-Mendoza | A61N 5/0622 |
| 2017/0361069 | A1 | 12/2017 | Gazzani Romolo et al. | |
| 2018/0304055 | A1 * | 10/2018 | Christopher | A61M 27/006 |
| 2019/0307997 | A1 | 10/2019 | Auvray et al. | |
| 2020/0375745 | A1 * | 12/2020 | Sampath | A61F 2/2875 |

FOREIGN PATENT DOCUMENTS

| | | | |
|---|---|---|---|
| CA | 2382871 | A1 | 3/2001 |
| CA | 2462367 | A1 | 9/2004 |
| CA | 2516175 | A1 | 9/2004 |
| CN | 1370086 | A | 9/2002 |
| CN | 101715355 | A | 5/2010 |
| CN | 103598883 | A | 2/2014 |
| DE | 2503990 | A1 | 8/1975 |
| DE | 69325384 | T2 | 7/1999 |
| DE | 602004019328.3 | | 2/2004 |
| DE | 602004015358.3 | | 3/2004 |
| DE | 102004020856 | A1 | 4/2005 |
| DE | 202012006700 | U1 | 8/2012 |
| DE | 202013002567 | U1 | 5/2013 |
| EP | 0135991 | A1 | 4/1985 |
| EP | 0798011 | A1 | 10/1997 |
| EP | 1207931 | A2 | 5/2002 |
| EP | 1248556 | A2 | 10/2002 |
| EP | 1596895 | A2 | 11/2005 |
| EP | 1649880 | A2 | 4/2006 |
| EP | 2019699 | A1 | 2/2009 |
| FR | 2695564 | A1 | 3/1994 |
| FR | 2698535 | A1 | 6/1994 |
| FR | 2746658 | A1 | 10/1997 |
| JP | H02193674 | A | 7/1990 |
| JP | 2003507140 | A | 2/2003 |
| JP | 2006517850 | A | 8/2006 |
| JP | 4566595 | B2 | 10/2010 |
| JP | 5701469 | B2 | 4/2015 |
| KR | 101012605 | B1 | 2/2011 |
| WO | 2021050881 | A1 | 3/2021 |

* cited by examiner

FIG. 3
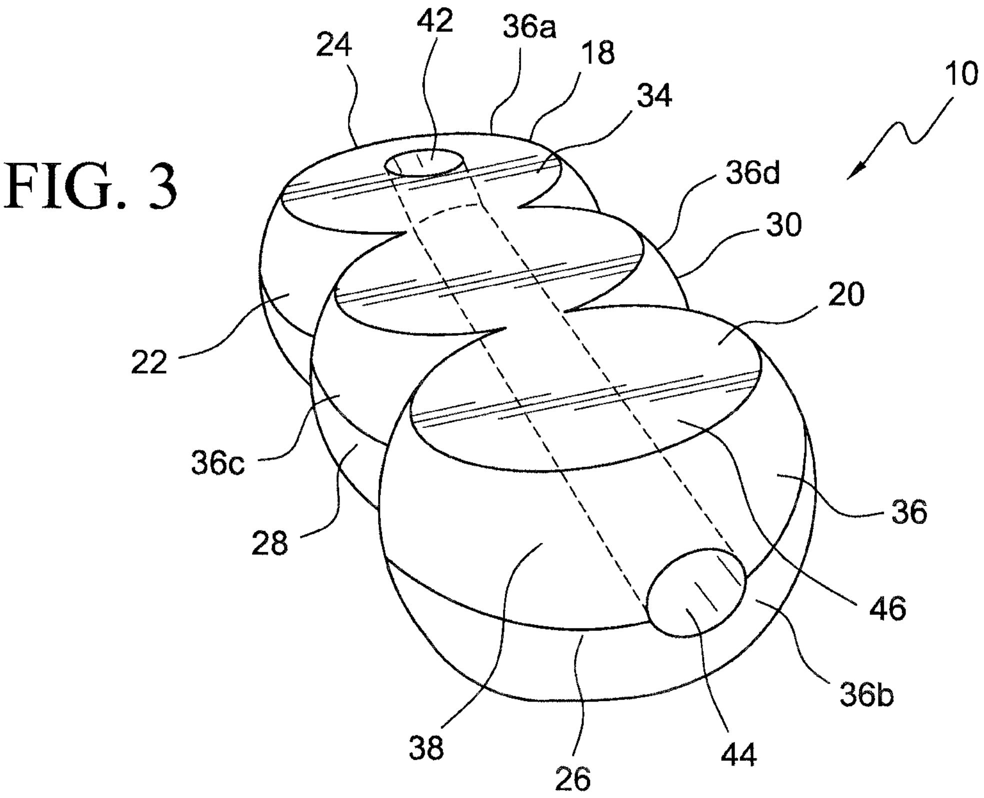
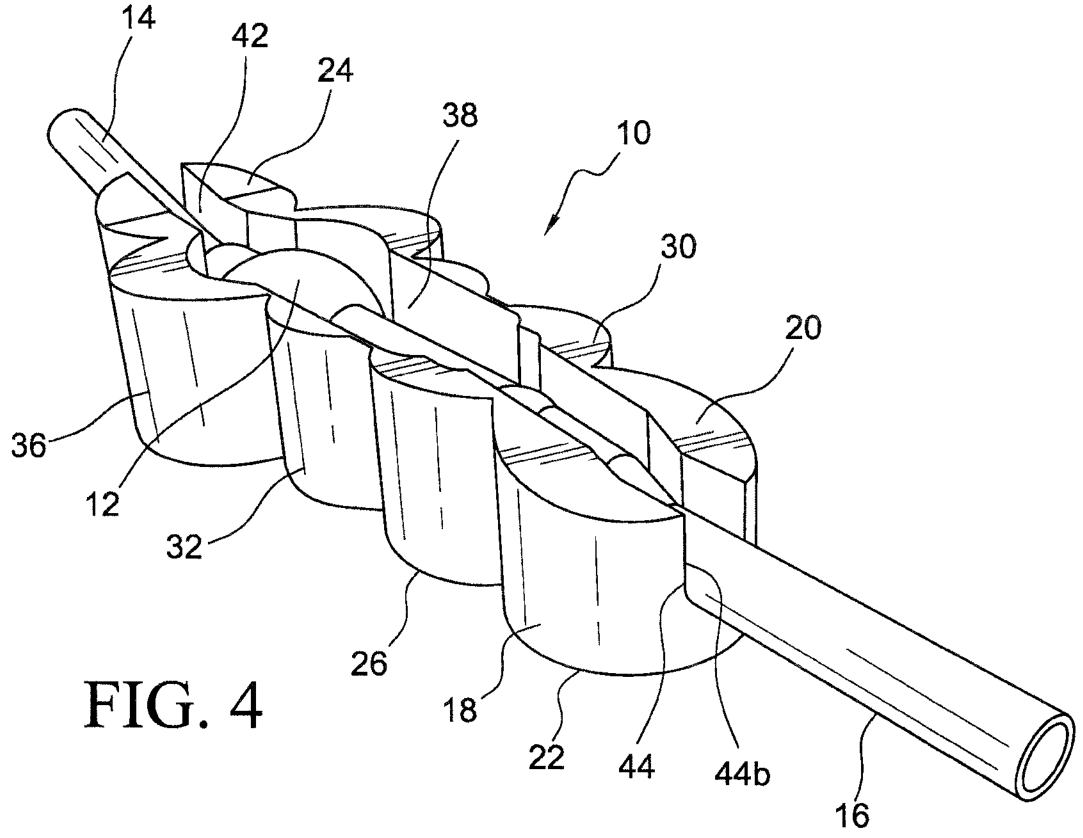
FIG. 4

CEREBRAL SPINAL FLUID SHUNT PLUG

CROSS REFERENCE TO RELATED APPLICATION

This application is a continuation of U.S. patent application Ser. No. 17/450,878, entitled "CEREBRAL SPINAL FLUID SHUNT PLUG," filed Oct. 14, 2021, which claims the benefit of U.S. Provisional Application Ser. No. 63/092,606, entitled "CEREBRAL SPINAL FLUID SHUNT PLUG," filed Oct. 16, 2020, and U.S. patent application Ser. No. 17/450,878, entitled "CEREBRAL SPINAL FLUID SHUNT PLUG," filed Oct. 14, 2021 is also a continuation in part of U.S. patent application Ser. No. 16/662,624, entitled "CEREBRAL SPINAL FLUID SHUNT PLUG," filed Oct. 24, 2019, which is a continuation in part of U.S. patent application Ser. No. 15/830,529, entitled "CEREBRAL SPINAL FLUID SHUNT PLUG," filed Dec. 4, 2017, which claims the benefit of U.S. Provisional Patent Application Ser. No. 62/488,966, entitled "CEREBRAL SPINAL FLUID SHUNT PLUG," filed Apr. 24, 2017, which are incorporated herein by reference.

BACKGROUND OF THE INVENTION

1. Field of the Invention

The present invention relates to a cerebral spinal fluid shunt plug.

2. Description of the Related Art

Hydrocephalus is a condition in which an excessive accumulation of cerebral spinal fluid is encountered. Cerebral spinal fluid is the clear fluid that surrounds the brain and the spinal cord. The excessive accumulation results in abnormal dilation of the ventricles within the brain. This dilation may cause the accumulation of potentially harmful pressure on the tissues of the brain.

Hydrocephalus is most often treated through the utilization of a shunt system. Cerebral spinal fluid shunt systems divert the flow of cerebral spinal fluid from a site within the ventricles to another area of the body where the cerebral spinal fluid can be absorbed as part of the circulatory system.

Shunt systems are commonly installed by creating a small hole within the skull, commonly referred to as a burr hole. A ventricular catheter is passed through the burr hole and positioned in the ventricular space. A peritoneal catheter is positioned at another location within the body where the cerebral spinal fluid can be diverted and absorbed. For example, it is common to either shunt the cerebral spinal fluid from the cerebral ventricles to the peritoneal cavity for reabsorption into the blood through the peritoneum or the cerebral spinal fluid may be shunted from the cerebral ventricles into the right atrium of the heart where the cerebral spinal fluid is directly shunted into the blood circulation.

In accordance with a typical procedure, incisions are made for the ventricular catheter and the peritoneal catheter. The peritoneal catheter is then positioned, and a burr hole is formed within the skull. Thereafter, the ventricular catheter is positioned. The ventricular catheter and the peritoneal catheter are then connected to a shunt valve which controls the flow of cerebral spinal fluid from the ventricle, through the ventricular catheter, and to the peritoneal catheter. The incisions are then closed.

In addition to common complications, such as shunt malfunction, shunt failure, and shunt infection, the utilization of catheters passing through the burr hole with the shunt valve positioned between the skull and the scalp results in other problems. For example, the shunt valve may resorb bone thereby creating a defect in the skull. In addition, the shunt valve and/or ventricular catheter are susceptible to movement. Still further, the ventricular catheter is susceptible to kinks as it passes through and around the burr hole.

With the foregoing in mind, it is desirable to improve upon current techniques for the placement of cerebral spinal fluid shunt systems.

SUMMARY OF THE INVENTION

In an aspect a cerebral spinal fluid shunt plug includes a shunt plug housing having a shunt valve recess formed therein and a window recess with an access hole. The cerebral spinal fluid shunt plug also includes a shunt valve shaped and dimensioned for positioning within the shunt valve recess of the shunt plug housing and a window shaped and dimensioned for the positioning within the window recess of the shunt plug housing.

In some embodiments, the cerebral spinal fluid shunt plug includes access holes or passageways allowing the shunt valve recess to communicate with an exterior of the shunt plug housing, the access holes or passageways being shaped and dimensioned to allow for connection of a ventricular catheter and a peritoneal catheter with the shunt valve housed within the recess of the shunt plug housing.

In some embodiments, the cerebral spinal fluid shunt plug further includes an intracranial monitoring device recess with an access hole and an intracranial monitoring device shaped and dimensioned for the passage through the central access hole of the intracranial monitoring device recess.

In some embodiments, the central access hole extending from the window recess to a lower surface of the shunt plug housing is shaped and dimensioned for the passage of light, sound, and/or radio waves therethrough so as to access the brain for imaging and treatment.

In some embodiments, the window is optically transparent.

In some embodiments, the window is optically translucent to all light waves.

In some embodiments, the window is sonolucent.

In some embodiments, the window is radiolucent.

In some embodiments, the window is optically transparent, optically translucent to all light waves, is sonolucent, and is radiolucent.

In some embodiments, the window comprises polymethyl methacrylate (PMMA).

In some embodiments, the window is a lucent disk.

In some embodiments, the lucent disk includes an upper surface and a lower surface, and the curvature of the upper surface differs from the curvature of the lower surface.

In some embodiments, the lucent disk includes an alignment feature.

In some embodiments, the alignment feature includes a series of markings at different depths within the lucent disk.

In some embodiments, the series of markings includes an outer first lucent disk marking and an inner second lucent disk marking formed along the upper and lower surfaces, respectively, of the lucent disk.

In some embodiments, the series of markings further includes an interior lucent disk marking formed within a body of the lucent disk and in alignment with the outer first lucent disk marking and an inner second lucent disk marking.

In some embodiments, the lucent disk includes channels.

In another aspect a cerebral spinal fluid shunt plug assembly includes a shunt plug housing having a shunt valve recess and a shunt valve shaped and dimensioned for positioning within the shunt valve recess of the shunt plug housing. A lucent element is shaped and dimensioned for positioning adjacent to the shunt plug housing.

In some embodiments, the lucent element is a clear custom intercranial implant.

In some embodiments, the clear custom intercranial implant includes an implant body having an outer first surface, an inner second surface, and a peripheral edge extending between the outer first surface and the inner second surface.

In some embodiments, the lucent element includes an implant body with the mating segment formed with a relatively concave profile shaped and dimensioned to mate with the shunt plug housing.

In some embodiments, the mating segment includes a concave cut-out along a central segment thereof.

In a further aspect a cerebral spinal fluid shunt plug includes a shunt plug housing having a shunt valve recess formed therein and an intracranial monitoring device recess with an access hole. The shunt plug also includes a shunt valve shaped and dimensioned for positioning within the shunt valve recess of the shunt plug housing and an intracranial monitoring device shaped and dimensioned for the passage through the central access hole of the shunt plug housing.

In some embodiments, the intracranial monitoring device is a wireless intracranial monitoring device.

In some embodiments, the intracranial monitoring device includes a probe that passes through the access hole.

In some embodiments, the shunt plug housing includes access holes or passageways allowing the recess to communicate with an exterior of the shunt plug housing, the access holes or passageways being shaped and dimensioned to allow for connection of a ventricular catheter and a peritoneal catheter with the shunt valve housed within the shunt valve recess of the shunt plug housing.

Other advantages of the present invention will become apparent from the following detailed description when viewed in conjunction with the accompanying drawings, which set forth certain embodiments of the invention.

BRIEF DESCRIPTION OF THE DRAWINGS

FIG. 3 is a perspective view of the shunt plug housing of the present invention with alternate positions for the access apertures.

FIGS. 4, 5, and 6 are sectional views of the shunt plug, including the shunt plug housing, the shunt valve, and the catheters, wherein the top portion of the shunt plug housing has been cut away to more clearly show the shunt valve.

DESCRIPTION OF THE PREFERRED EMBODIMENTS

Figure 1:
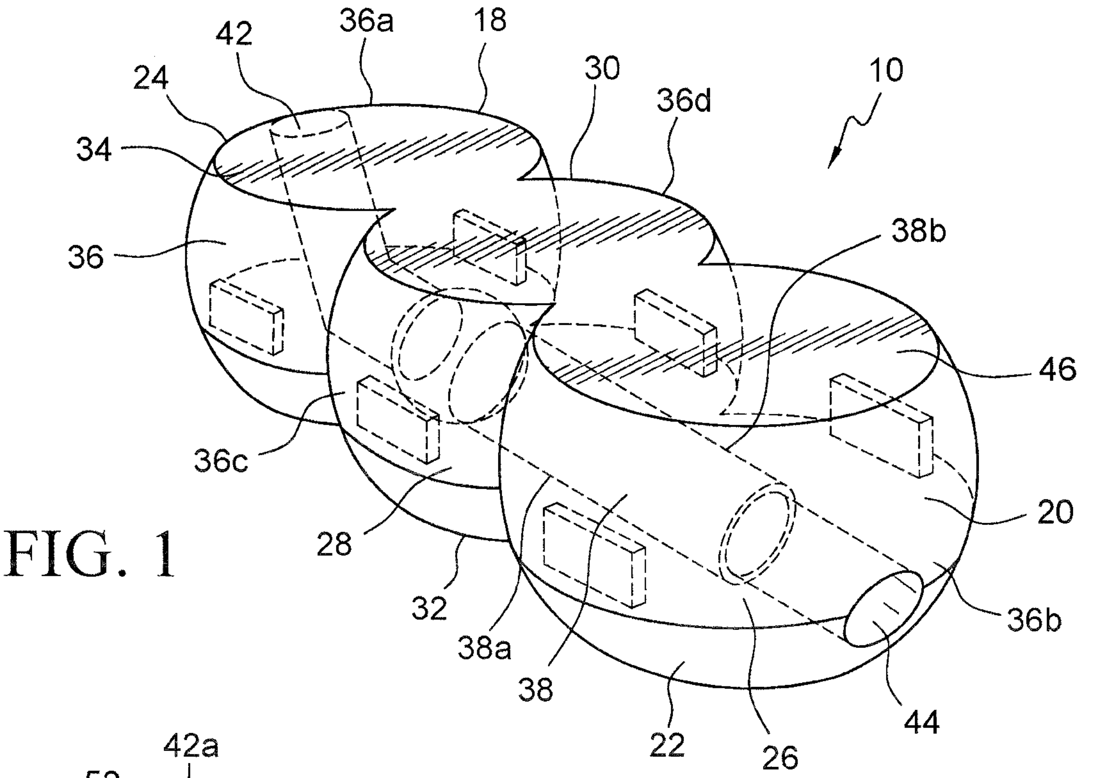
FIG. 1 is a perspective view of a shunt plug housing for a shunt plug in accordance with the present invention.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 7, various embodiments of a cerebral spinal fluid shunt plug 10 are disclosed in accordance with the present invention. It should be appreciated similar reference numerals are used for the various different embodiments. The shunt plug 10 is shaped and dimensioned for positioning within a physician formed cranial hole 100. The shunt plug 10 is further shaped and dimensioned for housing a shunt valve 12 in a reliable and secure manner so that a ventricular catheter 14 and peritoneal catheter 16 may be positioned without fear that the shunt valve 12 might move and/or the catheters 14, 16 might become disengaged from their desired locations.

The shunt plug 10 includes a shunt plug housing 18 composed of a bottom first housing member 20 and a top second housing member 22. The bottom first housing member 20 and top second housing member 22 are shaped and dimensioned for mating so as to define the shunt plug housing 18 in which the shunt valve 12 is positioned. In accordance with the disclosed embodiments, the shunt valve 12 will be placed within the shunt plug housing 18, so as to create the shunt plug 10 of the present invention, at the time of surgery. Further, in accordance with a disclosed embodiment the shunt plug housing is made of HDPE, although it is appreciated other materials may be used without departing from the spirit of the present invention.

The shunt plug housing 18, when the first housing member 20 and the second housing member 22 are connected together as shown with reference to FIGS. 1 and 3, includes a first end 24, a second end 26, a first lateral side 28, and a second lateral side 30. The shunt plug housing 18 also includes an upper surface 32, a lower surface 34, and a continuous side wall 36 extending between the upper surface 32 and the lower surface 34, as well as about the periphery of the shunt plug housing 18.

In accordance with the disclosed embodiments, and considering the procedure discussed below in greater detail, the shunt plug housing 18 is structured with consecutive and overlapping cylinders (for example, three cylinders as shown with reference to FIGS. 1, 2, and 3 and six cylinders as disclosed with reference to FIGS. 4, 5, and 6). While a shape in accordance with the disclosed embodiment is disclosed herein for the purpose of explaining the present invention, it is appreciated various shapes may be employed within the spirit of the present invention. As will be appreciated after reading the installation procedure presented below, the consecutive and overlapping cylinder structure was selected as a means of optimizing the installation procedure based upon the utilization of a single trephine to create consecutive and overlapping burr holes that ultimately define the cranial hole 100 in which the shunt plug 10 is positioned. As such, the shape of the shunt plug and the mechanism for the creation of the cranial hole are intimately related and may be varied based upon various needs and requirements.

Figure 2:
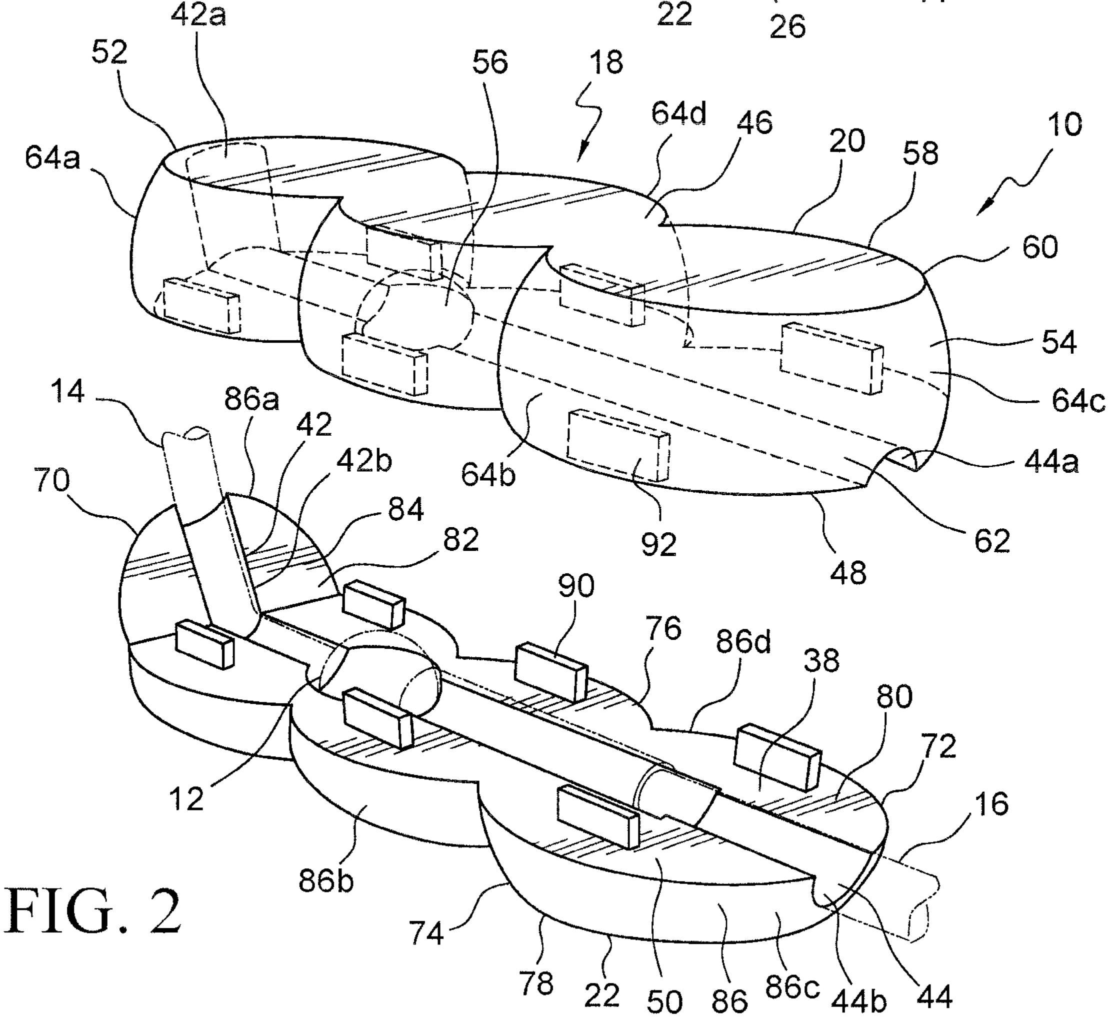
FIG. 2 is an exploded view of the shunt plug housing shown in FIG. 1.

Considering the embodiment disclosed with reference to FIGS. 1, 2, and 3, the side wall 36 of the disclosed embodiment is formed with a scalloped shape wherein a plurality of arcuate segments extends about the periphery of the shunt plug housing 18. The arcuate segments 36*a*, 36*b* at the first end 24 and the second end 26 of the shunt plug housing 18 define an arcuate surface of approximately 220 degrees to 320 degrees, and the arcuate segments 36*c*, 36*d* located at the center of the side wall 36 along the first and second lateral sides 28, 30 define an arc of approximately 40 to 140 degrees. In accordance with a preferred embodiment, the outer surface of the side wall 36 may be bowed outwardly so as to define a convex outer surface.

Figure 5:
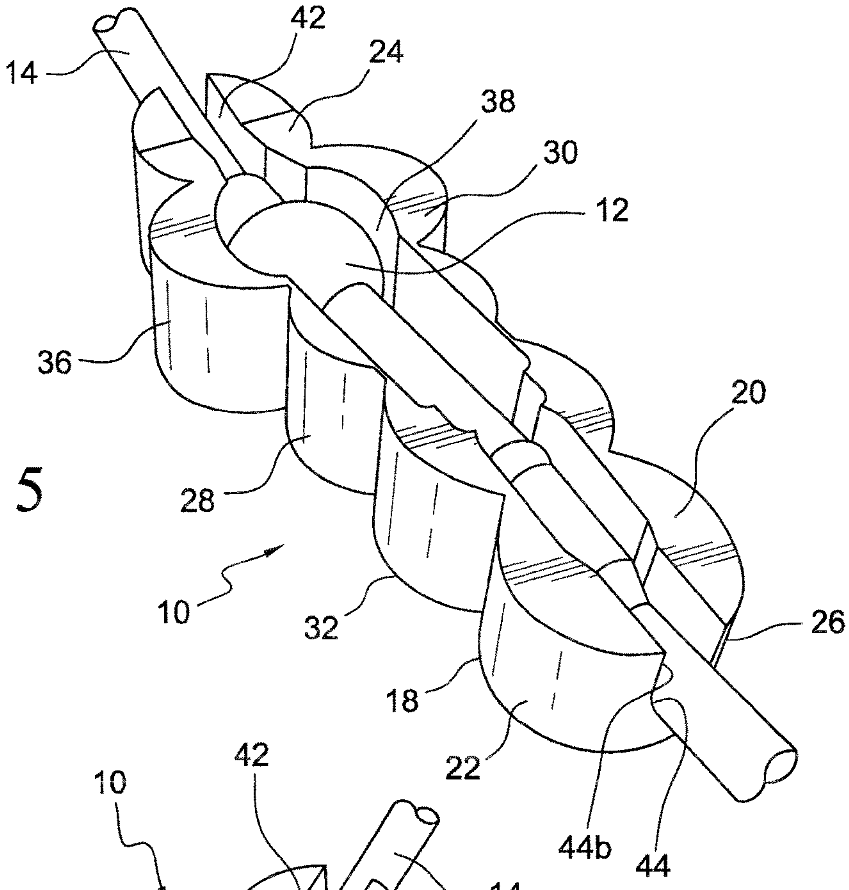
Figure 6:
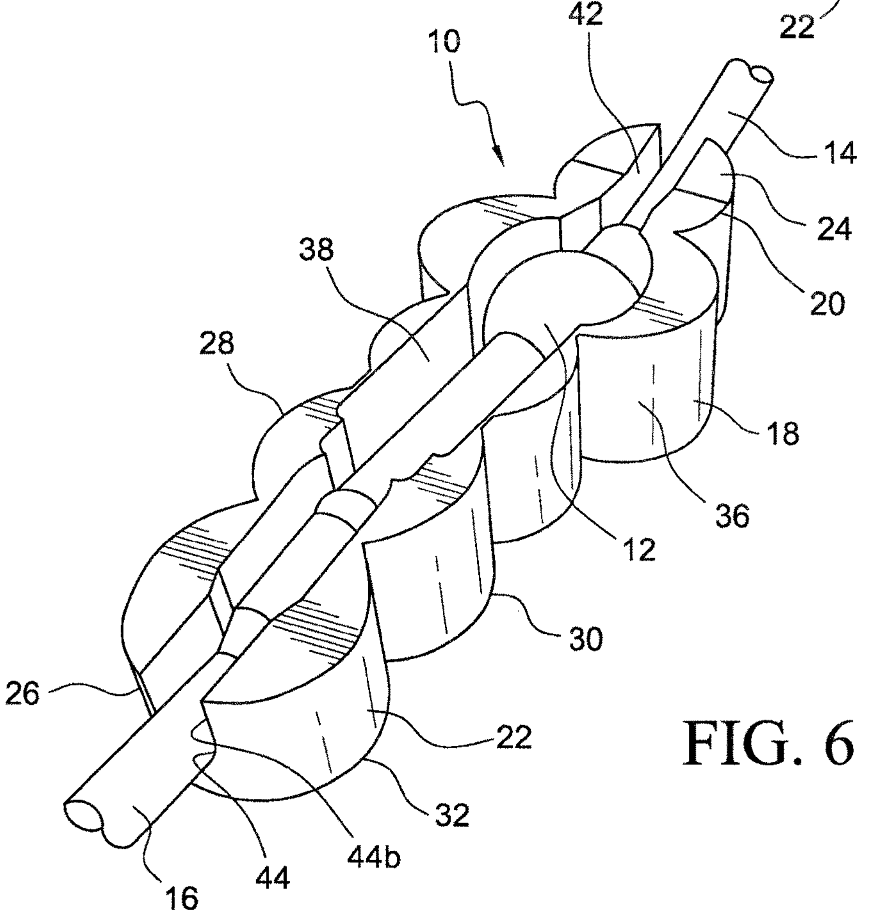

The embodiment disclosed with reference to FIGS. 4, 5, and 6 is similarly shaped but includes additional arcuate surfaces requiring die formation of additional burr holes during the installation process. In particular, the shunt plug 10 disclosed in FIGS. 4, 5, and 6 would require the formation of six burr holes in a highly specific pattern. The pattern employed creates a larger area for accommodating the needs of shunt valves having larger dimensions.

A recess 38 is formed within the shunt plug housing 18. The recess 38 is defined by recessed surfaces 38*a*, 38*b* formed along the surfaces of the first housing member 20 and the second housing member 22. The recess 38 is in communication with the exterior of the shunt plug housing 18 via access holes 42, 44 extending from the exterior surface of the shunt plug housing 18 to the recess 38. As will be explained below in greater detail, these access holes 42, 44 allow for connection of the ventricular catheter 14 and the peritoneal catheter 16 with the shunt valve 12 housed within the recess 38 of the shunt plug housing 18. As with the recess 38, the access holes 42, 44 are defined by recessed surfaces 42*a*, 42*b*, 44*a*, 44*b* formed along the surfaces of the first housing member 20 and the second housing member 22. Depending upon the shape of the shunt plug housing 18 and the shunt valve 12 to be positioned therein, the position of the access holes 42, 44 may be varied to optimize the ultimate positioning of the peritoneal catheter 16 and the ventricular catheter 14 (see, for example, FIGS. 1 and 3).

In particular, and with reference to FIG. 2, the first housing member 20 includes an exterior surface 46 that defines the exterior surface of the shunt plug housing 18 when the first and second housing members 20, 22 are connected together (as shown in FIG. 1) to form the complete shunt plug housing 18. The first housing member 20 also includes a mating surface 48 that engages the mating surface 50 of the second housing member 22 when the first and second housing members 20, 22 are connected together to form the complete shunt plug housing 18.

With this in mind, the first housing member 20 includes a first end 52, a second end 54, and first and second lateral sides 56, 58. The first housing member 20 also includes a top surface 60 defining the lower surface 34 of the shunt plug housing 18, a lower surface 62 that forms part of the mating surface 48 of the first housing member 20 that mates with the mating surface 50 of the second housing member 22 so as to define the junction of the first housing member 20 and the second housing member 22, as well as the recess 38 in which the shunt valve 12 is positioned. The first housing member 20 also includes side walls 64*a-d* extending between the top surface 60 and the lower surface 62. The side walls 64*b*, 64*c*, 64*d* at the first and second lateral sides 56, 58, as well as the second end 54, of the first housing member 20 define a portion of the exterior surface of the shunt plug housing 18. The side wall 64*a* at the first end 52 of the first housing member 20 forms part of the mating surface 48 of the first housing member 20 that mates with the mating surface 50 of the second housing member 22 so as to define the junction of the first housing member 20 and the second housing member 22.

The second housing member 22 includes a first end 70, a second end 72, and first and second lateral sides 74, 76. The second housing member 22 includes a top surface 78 defining the upper surface 32 of the shunt plug housing 18, a lower surface 80 that forms part of the mating surface 50 of the second housing member 22 that mates with the mating surface 48 of the first housing member 20 so as to define the junction of the first housing member 20 and the second housing member 22, as well as the recess 38 in which the shunt valve 12 is positioned. The second housing member 22 also includes an upwardly directed wall portion 82 extending upwardly from the lower surface 80 at the first end 70 of the second housing member 22. The wall portion 82 includes an interior surface 84 forming part of the mating surface 50 of the second housing member 22 that mates with the mating surface 48 of the first housing member 22 so as to define the junction of the first housing member 20 and the second housing member 22. In particular, the interior surface 84 of the wall portion 82 is shaped and dimensioned to mate with the side wall 64*a* at the first end 52 of the first housing member 20. The surface of the wall portion 82 opposite the interior surface 84 forms part of the side wall of the shunt plug housing 18 at the first end 24 of the shunt plug housing 18.

The second housing member 22 also includes side walls 86*a-d* extending between the lower surface 80 and the top surface 78. The side walls 86*a-d* at the first and second lateral sides 74, 76, as well as the first and second ends 70, 72, of the second housing member 22 define a portion of the exterior surface of the shunt plug housing 18.

Mating of the first housing member 20 with the second housing member 22 is further facilitated by the provision of protrusions 90 along the lower surface 80 of the second housing member 22 and matingly shaped indentations 92 along the lower surface 62 of the first housing member 20.

As discussed above, the recess 38 in which the shunt valve 12 is positioned, as well as the access holes 42, 44 for the passage of the ventricular and peritoneal catheters 14, 16, is formed within the shunt plug housing 18. The recess 38 and access holes 42, 44 are defined by recessed surfaces 38*a*, 38*b*, 42*a*, 42*b*, 44*a*, 44*b* formed along the surfaces of the first housing member 20 and the second housing member 22. In particular, the recessed surfaces 38*a*, 38*b*, 42*a*, 42*b* defining the recess 38 and the first access hole 42 are formed along the lower surface 80 of the second housing member 22 and the lower surface 62 of the first housing member 20. The recessed surfaces 44*a*, 44*b* defining the second access hole 44 are formed along the side wall 64*a* of the first housing member 20 at the first end 52 thereof and along the interior surface 84 of the wall portion 82 at the first end 70 of the second housing member 22.

With the foregoing description of the first housing member and the second housing member in mind, it is appreciated that the first and second housing members may take various shapes depending upon the desired inter-engagement of these two members when the shunt plug housing is fully formed and ready for use.

As briefly discussed above, the recess 38 defined within the shunt plug housing 18 is shaped and dimensioned for placement of the shunt valve 12 therein. As those skilled in the art will appreciate, a variety of shunt valves are known in the art and the present shunt plug housing 18 may be adapted to accommodate a variety of these shunt valves. For example, the following shunt valves may be used in conjunction with the present invention: CODMAN®/Integra HAKIM® and Certas Programmable Shunt Valve, MEDTRONIC® STRATA®, SOPHYSA® POLARIS®, Ascuelap proGAV®, and INTEGRA® OSV II®. The present invention may also be used in conjunction with the Rickam reservoir and other similar reservoirs used in cerebral spinal fluid management. In accordance with a preferred embodiment, the shunt plug housing 18 should have a surface area along its upper surface 32 of at least five $cm^2$ so as to accommodate various shunt valves and to provide the necessary space for placement of the shunt valve 12 within the recess 38 defined within the shunt plug housing 18.

Once the shunt valve 12 is positioned between the first housing member 20 and the second housing member 22 within the recess 38 defined thereby, the first housing member 20 may be connected to the second housing member 22 so as to fully enclose the shunt valve 12 therein. Thereafter, the shunt plug 10 of the present invention may be utilized for the purpose of performing a cerebral spinal fluid shunt procedure.

In accordance with yet another embodiment of the present invention as shown with reference to FIGS. 9 to 18 (which shows this embodiment in various shapes to accommodate shunt valves from various manufacturers), the shunt plug is structured such that the shunt valve is uncovered. In particular, and as with the previous embodiment, the shunt plug 210 is shaped and dimensioned for housing a shunt valve 212 in a reliable and secure manner so that a ventricular catheter 214 and peritoneal catheter 216 may be positioned without fear that the shunt valve 212 might move and/or the catheters 214, 216 might become disengaged from their desired locations.

The shunt plug 210 includes a shunt plug housing 218 composed of a bottom first housing member 220. In accordance with the disclosed embodiments, the shunt valve 212 will be placed within the shunt plug housing 218, so as to create the shunt plug 210 of the present invention, at the time of surgery.

Figure 15:
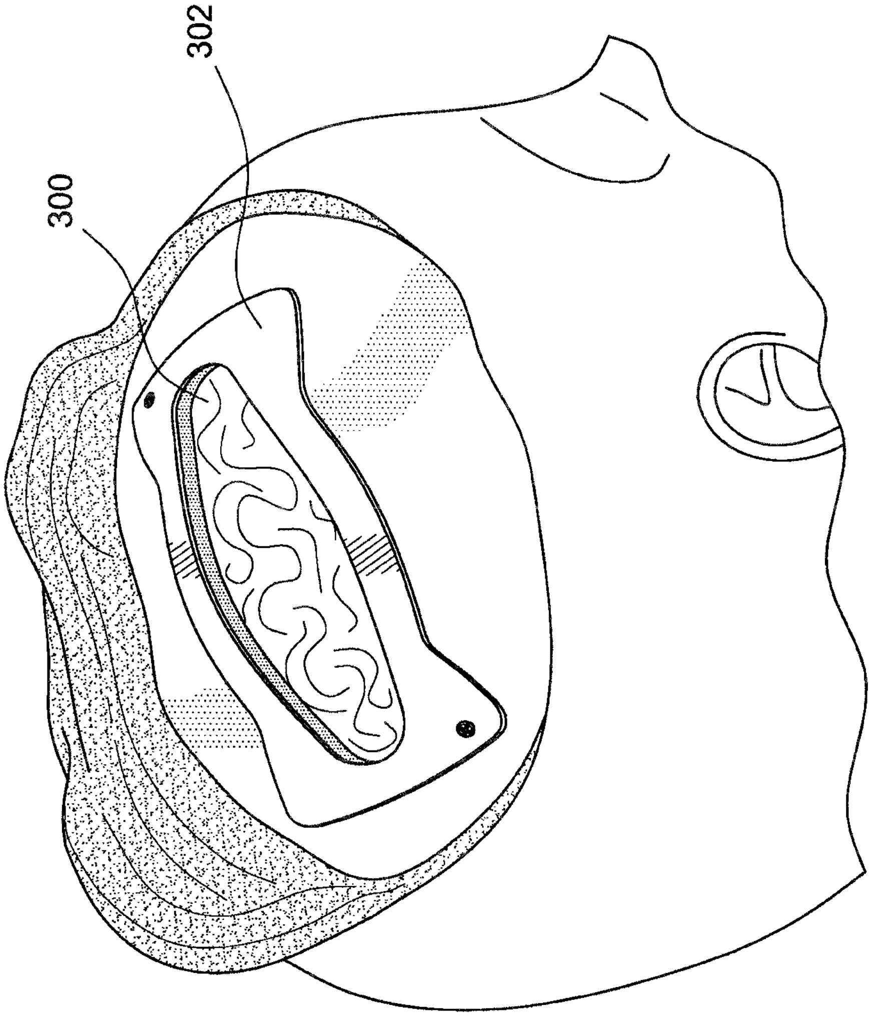
Figure 16:
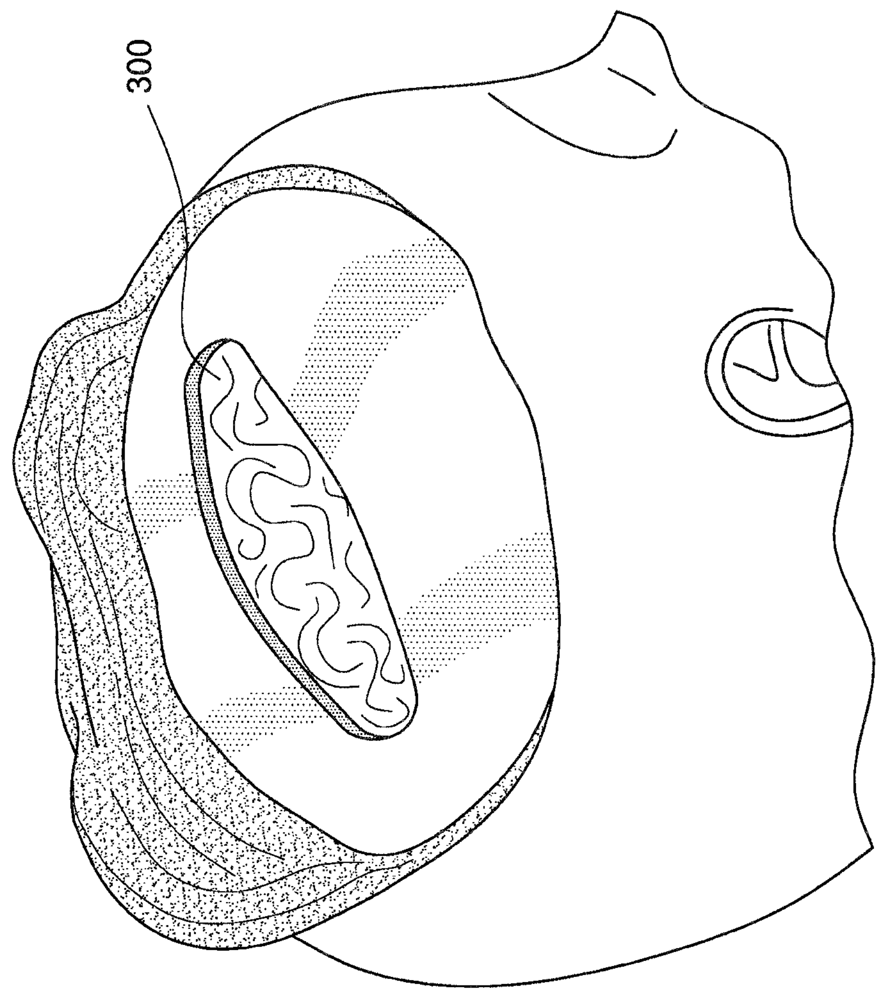
Figure 17:
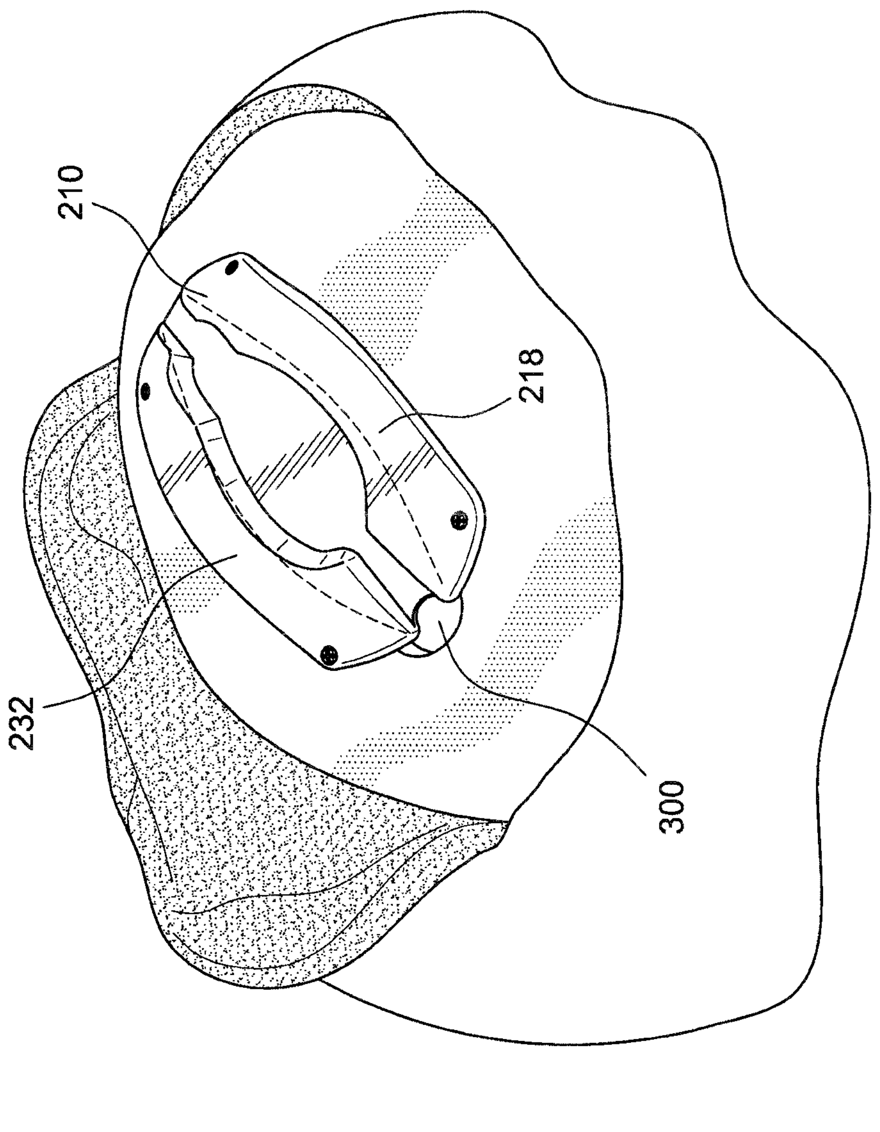
Figure 18:
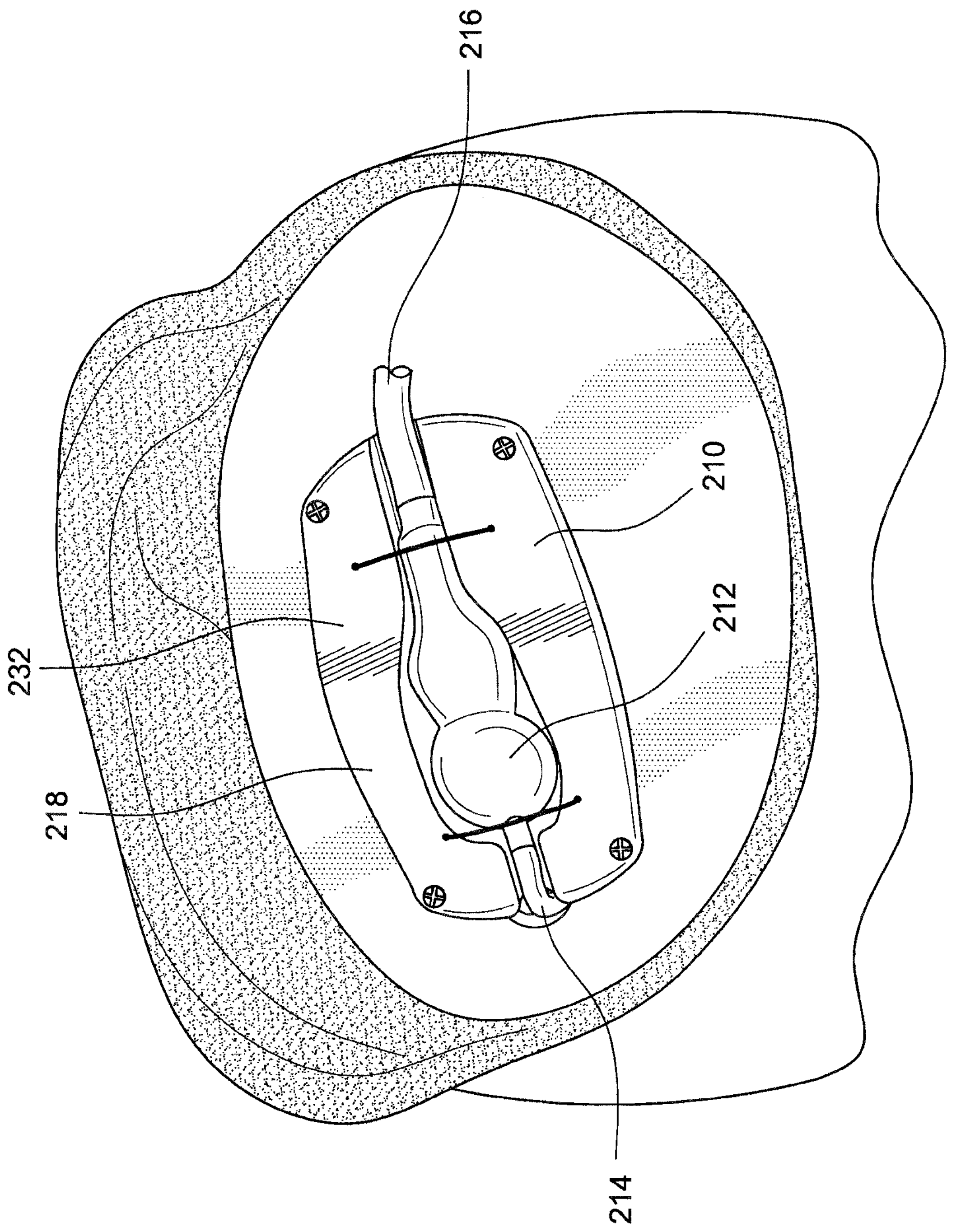

The shunt plug housing 218 includes a first end 224, a second end 226, a first lateral side 228, and a second lateral side 230. The shunt plug housing 218 also includes an upper surface 232, a lower surface 234, and continuous side walls 236*a-d* extending between the upper surface 232 and the lower surface 234, as well as about the periphery of the shunt plug housing 218. As will be appreciated based upon the following disclosure, the lower surface 234 is provided with a projection 234*p* that ultimately fits within the cranial hole 300 to assist in holding the shunt plug 210 in position after installation. With this in mind, the projection 234*p* is elliptically shaped to fit within the cranial hole 300 as shown in FIG. 15.

While particular shapes of the shunt plug housing 218 in accordance with the disclosed embodiment are disclosed herein for the purpose of explaining the present invention, it is appreciated various shapes may be employed within the spirit of the present invention. As such, the shape of the shunt plug and the mechanism for the creation of the cranial hole are intimately related and may be varied based upon various needs and requirements. For example, and in contrast with the embodiments described above with reference to FIGS. 1 to 6, the shunt plug housing includes a substantially elliptical shape.

A recess 238 is formed within the upper surface 232 of the shunt plug housing 218. The recess 238 is in communication with the exterior of the shunt plug housing 218 via access passageways 242, 244 extending from die exterior surface of the shunt plug housing 218 to the recess 238. As will be explained below in greater detail, these access holes (or passageways) 242, 244 allow for connection of the ventricular catheter 214 and the peritoneal catheter 216 with the shunt valve 212 housed within the recess 238 of the shunt plug housing 218. The access passageways 242, 244 are defined by recessed surfaces formed along the upper surface 232 of the shunt plug housing 218. Depending upon the shape of the shunt plug housing 218 and the shunt valve 212 to be positioned therein, the position of the access holes (or passageways) 242, 244 may be varied to optimize the ultimate positioning of the peritoneal catheter 216 and the ventricular catheter 214.

As discussed above, the recess 238 in which the shunt valve 212 is positioned, as well as the access holes 242, 244 for the passage of the ventricular and peritoneal catheters 214, 216, is formed within the shunt plug housing 218. The recess 238 and access holes 242, 244 are defined by recessed surfaces 238*a*, 242*a*, 244*a* formed along the upper surface 232 of the shunt plug housing 218. In particular, the recessed surface 238*a* defining the recess 238 is formed along the upper surface 232 of the shunt plug housing 218; the recessed surface 242*a* defining the first access hole (or passageway) 242 is formed along the upper surface 232 adjacent the first end 224; and the recessed surfaces 244*a* defining the second access hole (or passageway) 244 are formed along the side wall 264*a* of the shunt plug housing 218 at the second end 226 thereof.

As briefly discussed above, the recess 238 defined within the shunt plug housing 218 is shaped and dimensioned for placement of the shunt valve 212 therein. As those skilled in the art will appreciate, and as explained above in conjunction with the prior embodiment, a variety of shunt valves are known in the art and the present shunt plug housing 218 may be adapted to accommodate a variety of these shunt valves. The present invention may also be used in conjunction with the Rickam reservoir and other similar reservoirs used in cerebral spinal fluid management. In accordance with a preferred embodiment, the shunt plug housing 218 should have a surface area along its upper surface 232 of at least five $cm^2$ so as to accommodate various shunt valves and to provide the necessary space for placement of the shunt valve 212 within the recess 238 defined within the shunt plug housing 218.

Once the shunt valve 212 is positioned within the recess 238 of the shunt plug housing 218 the shunt plug 210 of the present invention may be utilized for the purpose of performing a cerebral spinal fluid shunt procedure.

Figure 7:
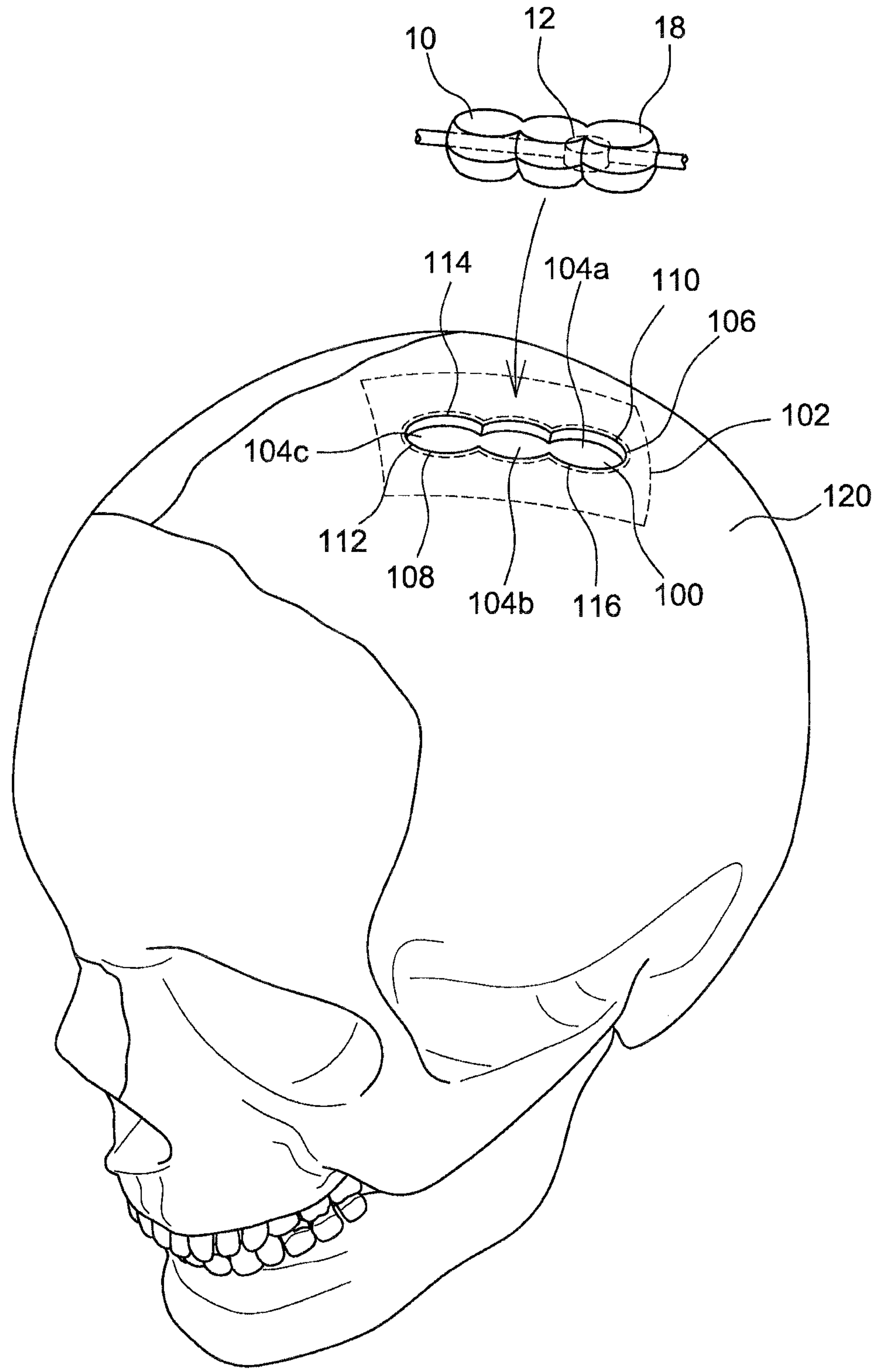
FIG. 7 is an exploded representative view of the installation process.

Referring to FIG. 7, and with particular reference to the embodiment disclosed in FIGS. 1, 2, and 3, the procedure is first initiated by making the required incision for passage of the peritoneal catheter 16. Thereafter, a cranial incision is made and the cranial hole 100 is created utilizing a template 102 (shown in broken lines) and predefined trephine (not shown). In contrast to prior art procedures, a singular burr hole is not formed. Rather, adjacent circular holes 104*a-c* (for example, three as shown in the disclosed embodiment) are formed creating the cranial hole 100 that is shaped for snuggly fitting the shunt plug 10 therein. As with the shape of the shunt plug 10, the cranial hole 100 created in accordance with the present invention includes scalloped edges. In particular, the cranial hole 100 includes first and second ends 106, 108 with an arcuate surface 110, 112 of approximately 220 to 320 degrees, as well as first and second lateral arcuate surfaces 114, 116 of approximately 40 to 140 degrees. Given the matching shape of the cranial hole 100 and the shunt plug 10, the shunt plug 10 will fit snugly within the cranial hole 100 thereby minimizing potential movement after completion of the procedure.

With the cranial hole 100 completed, the ventricular catheter 14 is positioned within the ventricle and the peritoneal catheter 16 is positioned with the body as using well know medical procedures. Thereafter, the ends of the peritoneal catheter 16 and the ventricular catheter 14 adjacent the shunt plug 10 may be secured to the shunt valve 12 housed within the shunt plug 10 by passing the ends of the respective catheters into die first and second access holes 42, 44 formed at locations along the exterior of the shunt plug housing 18. Thereafter, the shunt plug 10 is positioned within the cranial hole 100. The shunt plug 10 is mounted within the cranial hole 100 such that the upper surface 32 is substantially flush with the outer surface of the skull 120. It is, however, appreciated the exact positioning of the shunt plug will vary based upon specific anatomical characteristics of the patient. Once the shunt plug 10 is properly positioned, the shunt valve 12 is actuated utilizing well known procedures, and the procedure is completed in accordance with known medical procedures.

Figure 8:
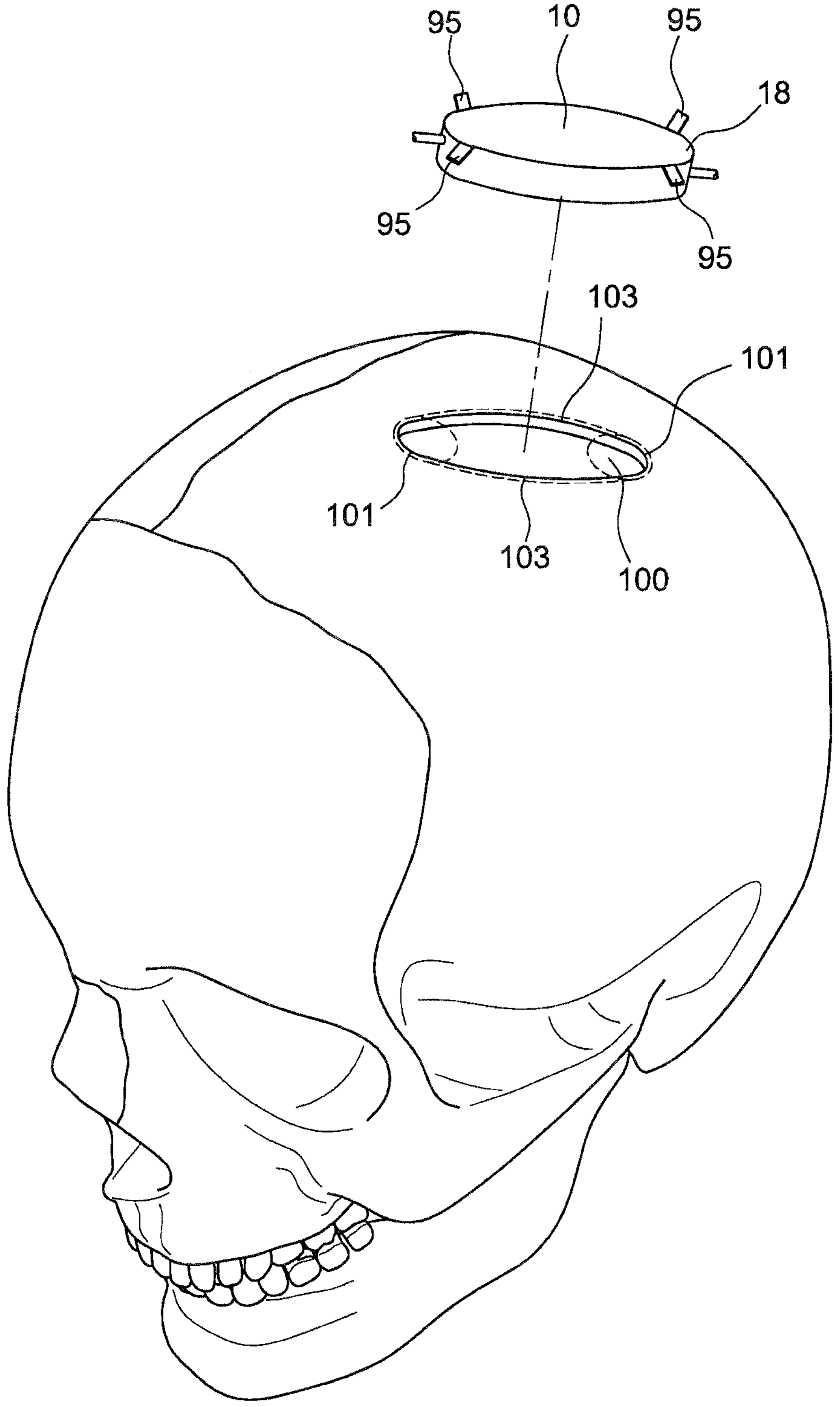
FIG. 8 is an exploded representative view of the installation process with a shunt plug of an alternate shape.
Figure 9:
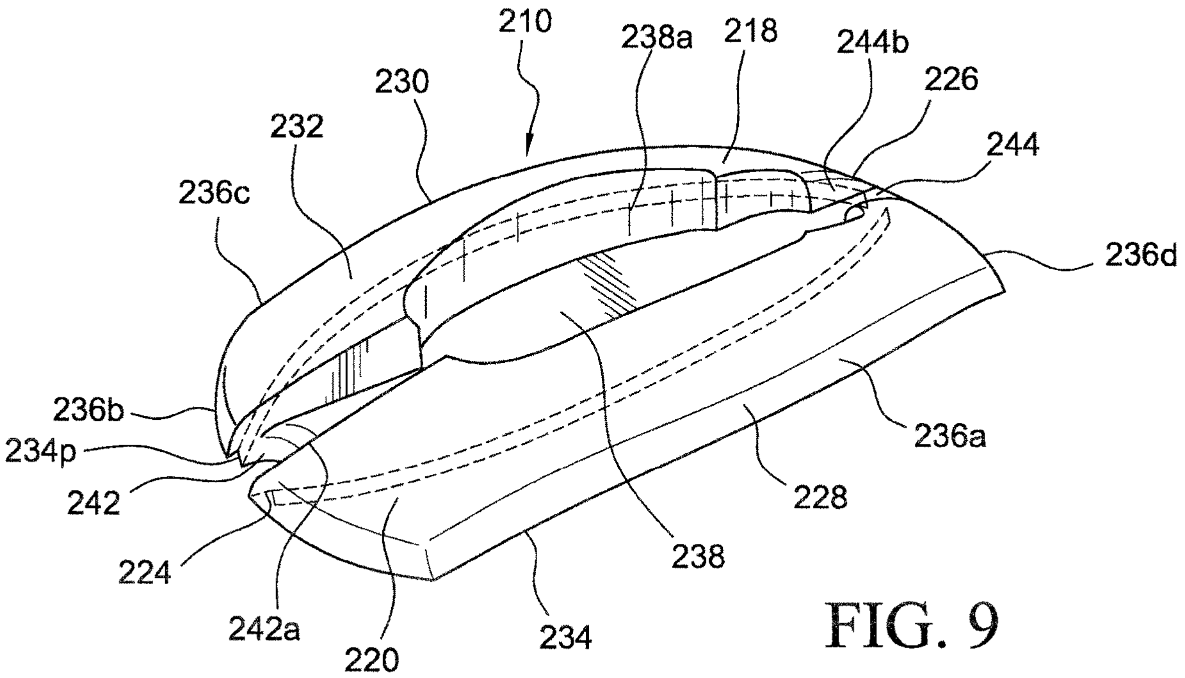
FIGS. 9, 10, and 11 are perspective views of a shunt plug housing in accordance with an alternate embodiment and showing three different cavity shapes for accommodating different shunt valves.
Figure 10:
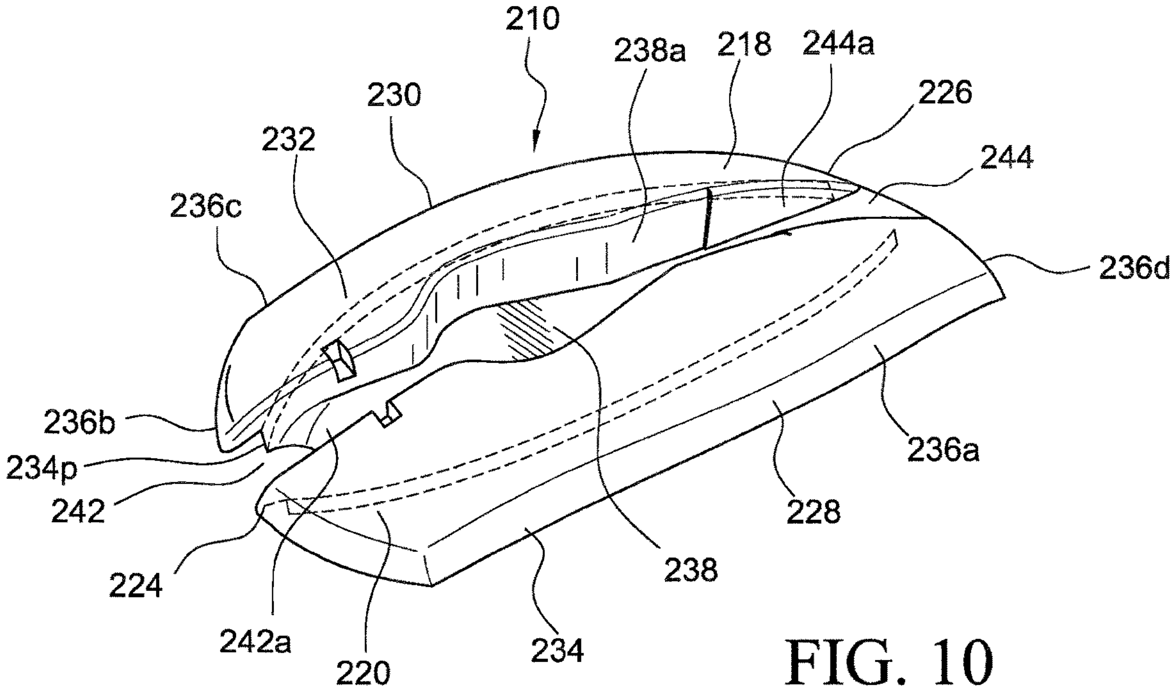
Figure 11:
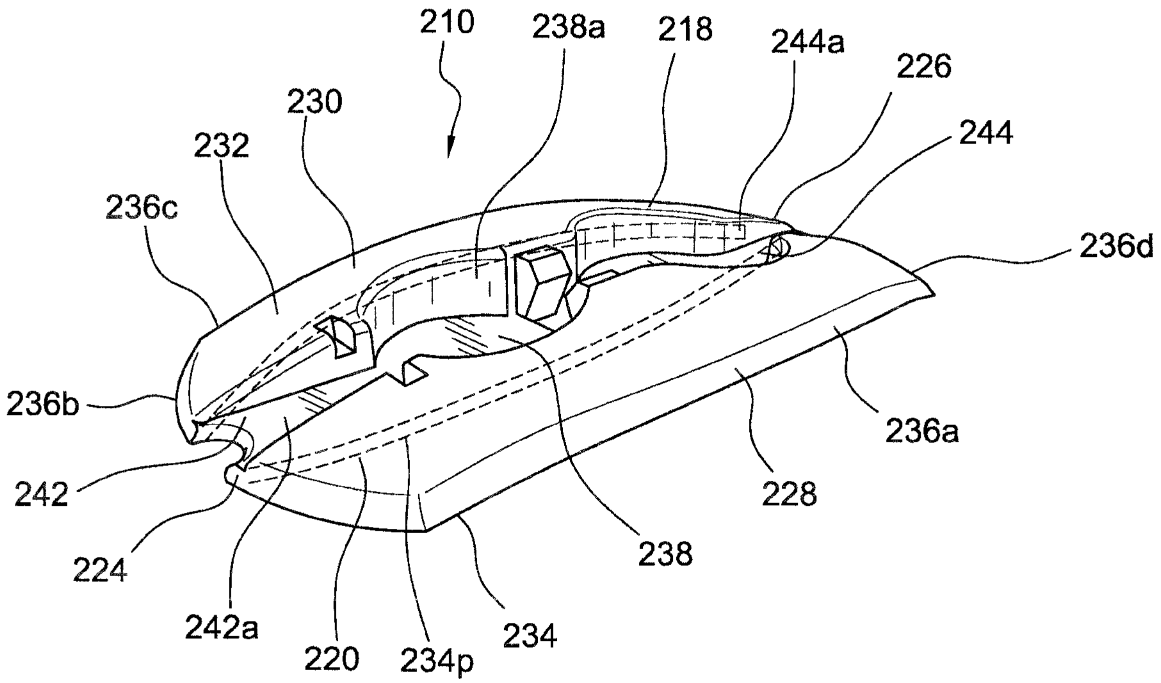
Figure 12:
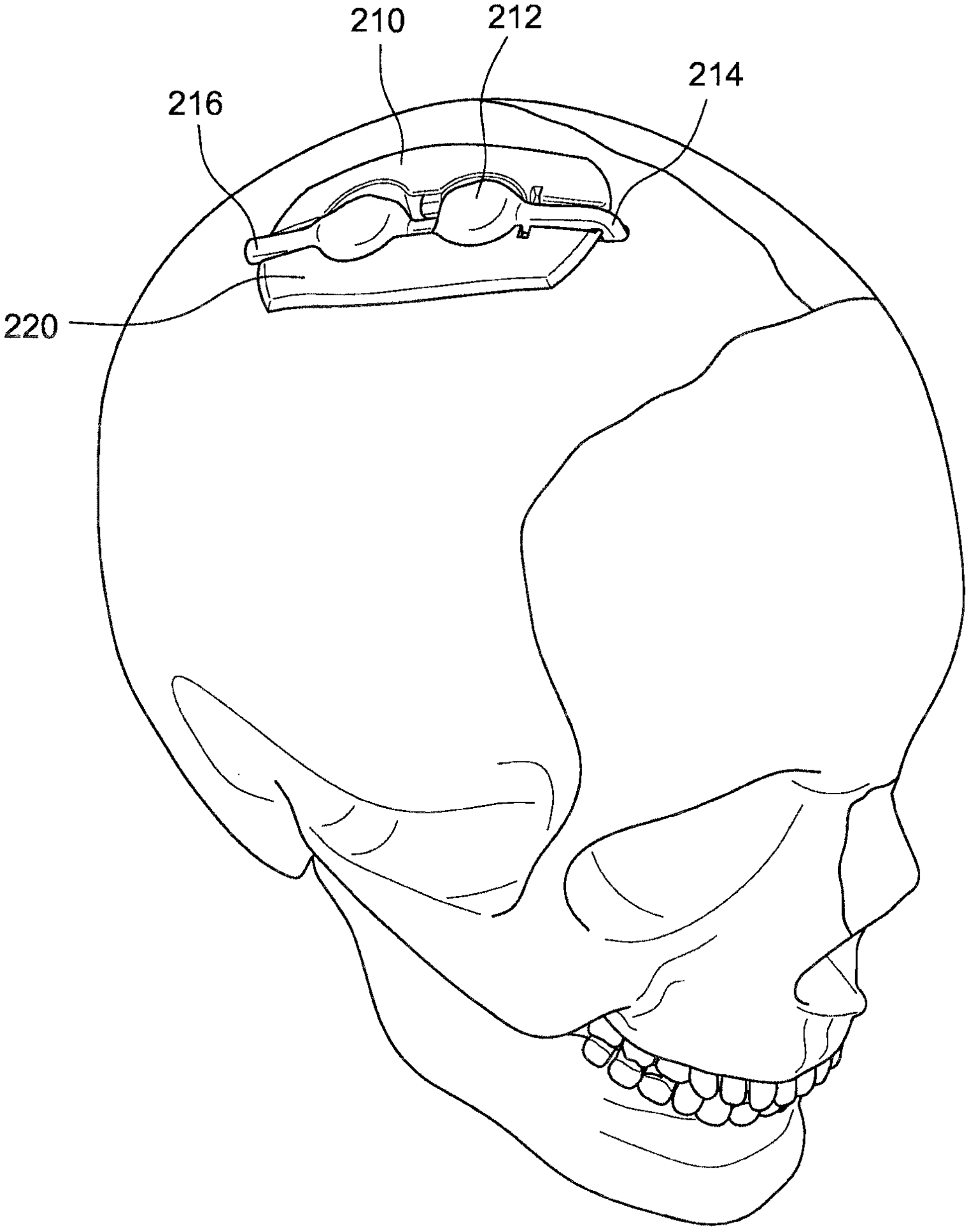
FIG. 12 is a perspective view of a cerebral spinal fluid shunt plug in accordance with the embodiment shown with reference to FIGS. 9, 10, and 11.
Figure 13:
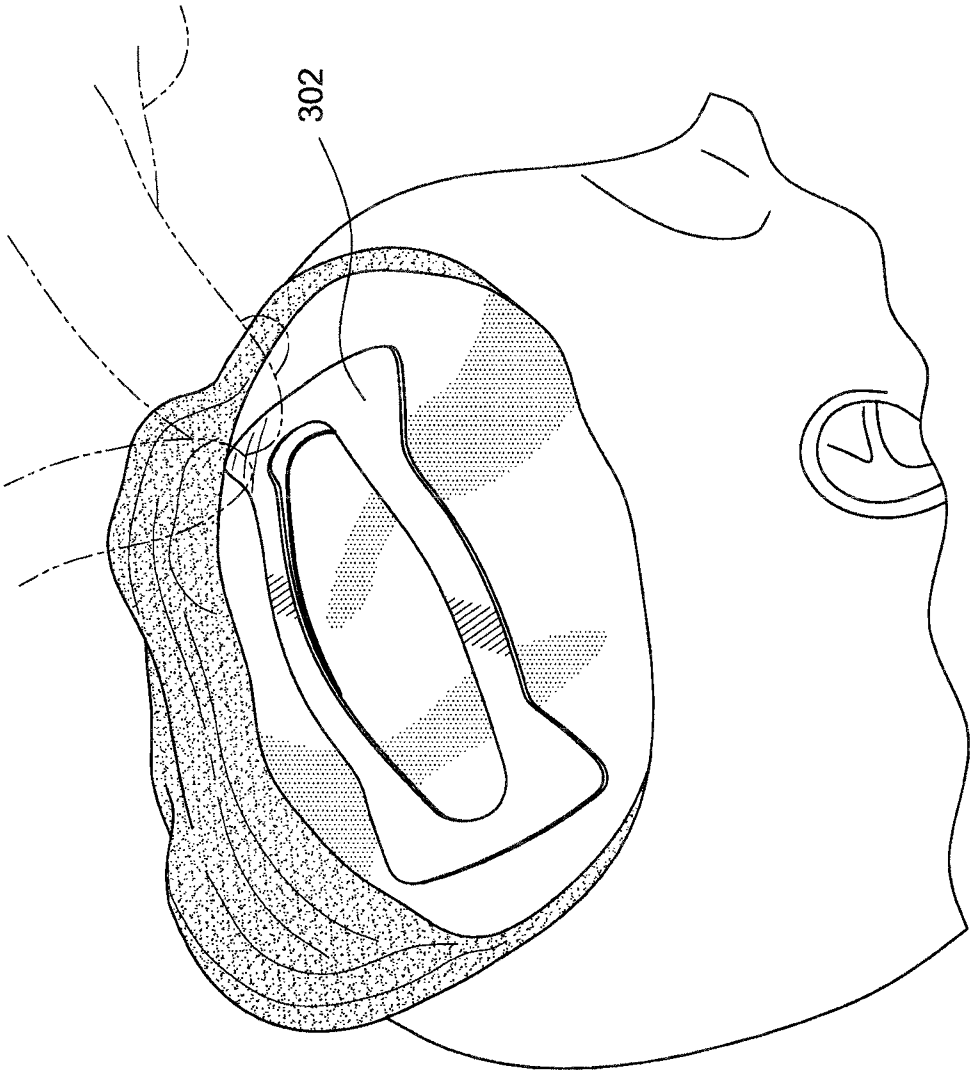
FIGS. 13 to 18 show the steps associated with the implantation of a cerebral spinal fluid shunt plug in accordance with the embodiment disclosed with reference to FIGS. 9, 10, and 11.
Figure 14:
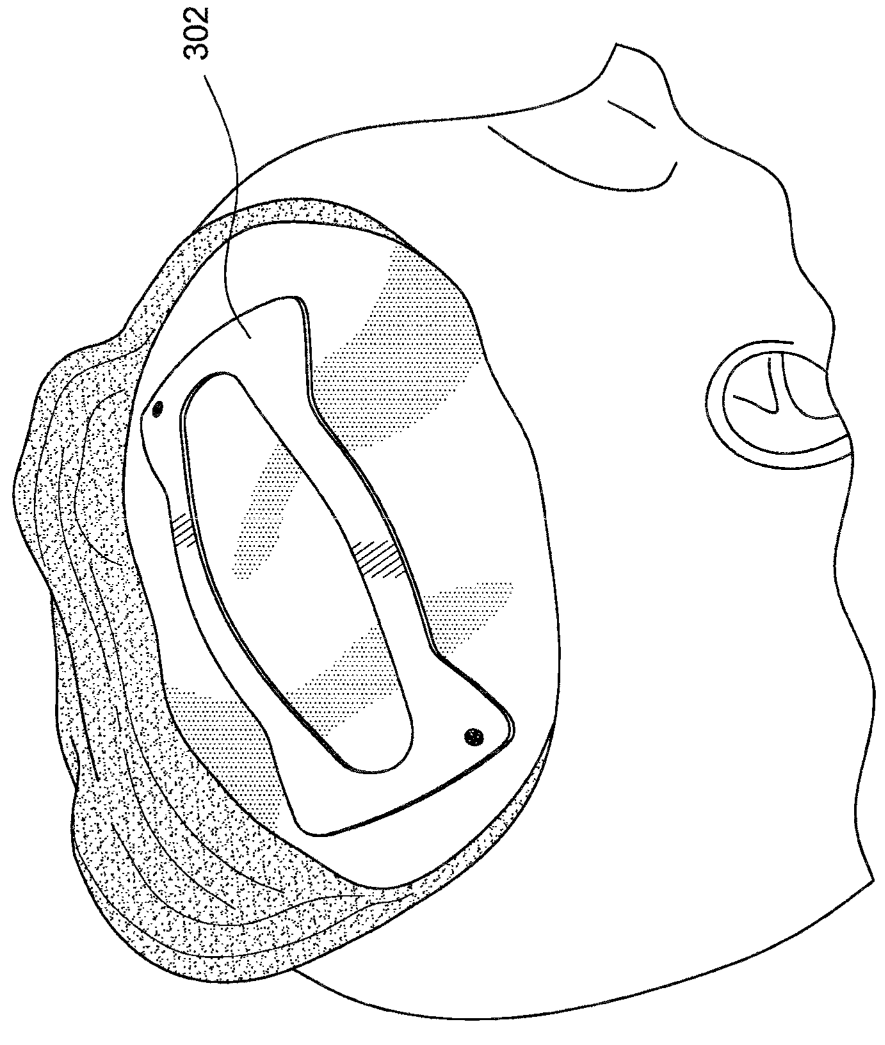

As discussed above, the shunt plug of the present invention may take various shapes. One possible shape where simplicity is considered to be important might involve an elliptically shaped shunt plug housing 18 as shown with reference to FIG. 8. Such an embodiment would require a cranial hole 100 formed by the creation of two burr holes 101 with two connecting cuts 103 made in the shape of the shunt plug 10 so as to allow for placement of the shunt plug 10 within the cranial hole 100. It is, however, appreciated die cranial hole may be made using any method of creating an elliptical craniectomy acceptable by those skilled in the art. When using such an embodiment, it is appreciated variations in the cuts 103 between the two burr holes 101 are likely, and the shunt plug 10 is therefore provided with a plurality of attachment tabs 95 that may be used to secure the shunt plug 10 to the area of the skull 120 immediately adjacent to the cranial hole 100.

Referring to FIGS. 13 to 18, and with particular reference to the embodiment disclosed in FIGS. 9 to 18, the procedure is first initiated by making the required incision for passage of the peritoneal catheter 216. Thereafter, a cranial incision is made and the cranial hole 300 in the skull 320 is created utilizing a template 302 (shown in broken lines). In accordance with a preferred embodiment, and considering the elliptical shape of the cranial hole 300, burr holes are formed at the respective ends of the template 302, and the remainder of the skull 320 is cut away along the lines as defined by the template 302. As with the prior embodiment, it is appreciated the cranial hole may be made using any method of creating an elliptical craniectomy acceptable by those skilled in the art. Given the matching shape of the cranial hole 300 and the shunt plug 210, the shunt plug 210 will fit snugly within the cranial hole 300 thereby minimizing potential movement after completion of the procedure.

With the cranial hole 300 completed, the ventricular catheter 214 is positioned within the ventricle and the peritoneal catheter 216 is positioned with the body as using well know medical procedures. Thereafter, the shunt plug housing 218 is positioned within the cranial hole 300 with the upper surface 232 facing upwardly, and the ventricular catheter 214 is cut to an appropriate length. The ends of the peritoneal catheter 216 and the ventricular catheter 214 adjacent the shunt plug 210 are then secured to the shunt valve 212 and the shunt valve 212 is positioned within the shunt plug housing 218. In particular, the shunt plug 210 is mounted within the cranial hole 300 such that the upper surface 232 is substantially flush with the outer surface of the skull 320 and the projection 234*p* along the lower surface 234 is positioned within the cranial hole 300. As such, portions along the periphery of the shunt plug housing 218 overlie the skull 320, and screws may be passed therethrough to facilitate secure attachment of the shunt plug 210 to the skull. It is, however, appreciated the exact positioning of the shunt plug will vary based upon specific anatomical characteristics of the patient. Once the shunt plug 210 is properly positioned and secured in place using known techniques, the shunt valve 212 is actuated utilizing well known procedures, and the procedure is completed in accordance with known medical procedures.

With the foregoing in mind, the present shunt plug offers multiple advantages. It eliminates mobility of the shunt valve and/or reservoir. As a result, the shunt valve location is known and will not migrate caudal, cephalad, anterior, or posterior which can cause challenges during revision surgery. The ventricular catheter is a precise distance from the shunt valve to the ventricle, therefore mobility of the shunt valve can displace the location of the ventricular catheter. The present shunt plug eliminates cranial deformity as it avoids the need to implant the shunt valve on top of the cranium and underneath the scalp. As a result, pressure on the scalp is minimized along with any accompanying complications such as pain or implant extrusion. In addition, the present shunt plug minimizes micro-motion; that is, the well documented fact that implant micro-motion can lead to bone resorption (causing further deformity) and can lead to infection. Finally, the present shunt plug minimizes catheter kinking as the sharpest angle in the catheter's pathway is the top of the perforator made burr hole and by controlling the angle of entry of the catheter, the risk of occlusion is minimized.

It is appreciated that once the cerebral spinal fluid shunt plug of the present invention is implanted within the cranium and covered by the scalp, it may be desirable to identify, for example, via triangulation, a specific point or points on the cerebral spinal fluid shunt plug, in particular, the shunt valve itself; for example, to identify and/or locate the center of the programmable portion of the programmable shunt valve or reservoir. To achieve this, and with reference to FIGS. 19 to 22, various embodiments are disclosed. It is appreciated these variations are disclosed in accordance with the embodiment described with reference to FIGS. 11 and 12, and the variations described herein may be applied to any of the embodiments disclosed herein.

Figure 19:
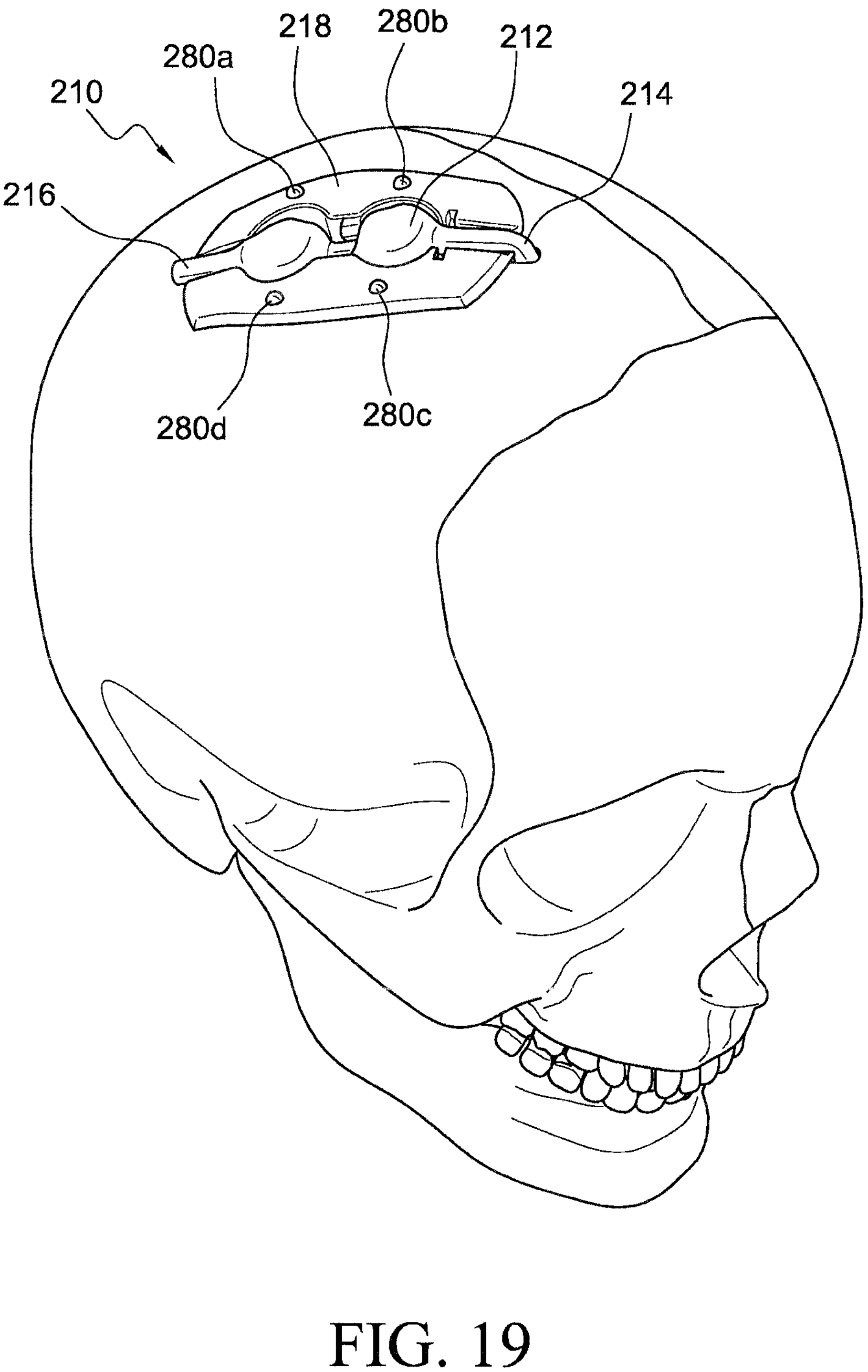
FIGS. 19, 20, 21, and 22 are perspective views of alternate embodiments of a cerebral spinal fluid shunt plug in accordance with the present invention.
Figure 20:
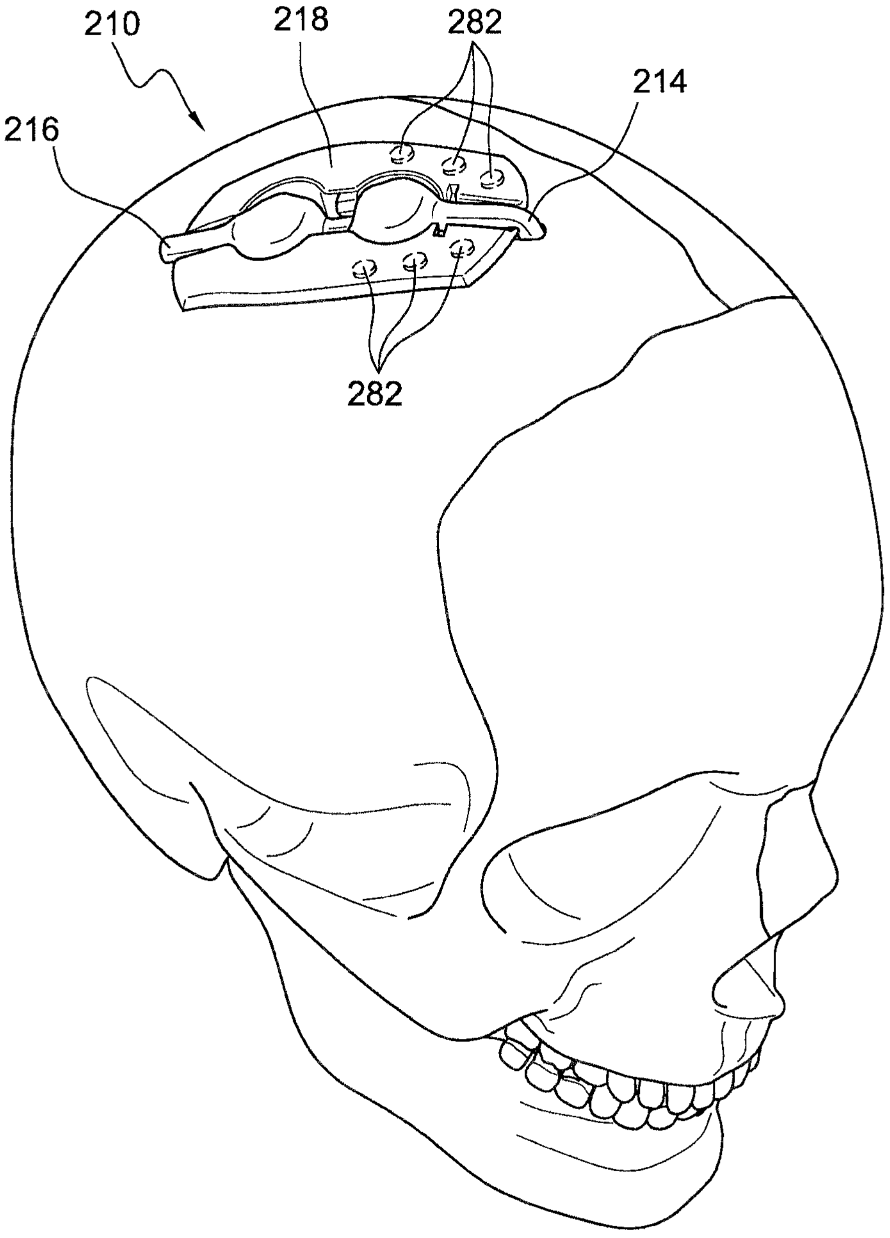
Figure 21:
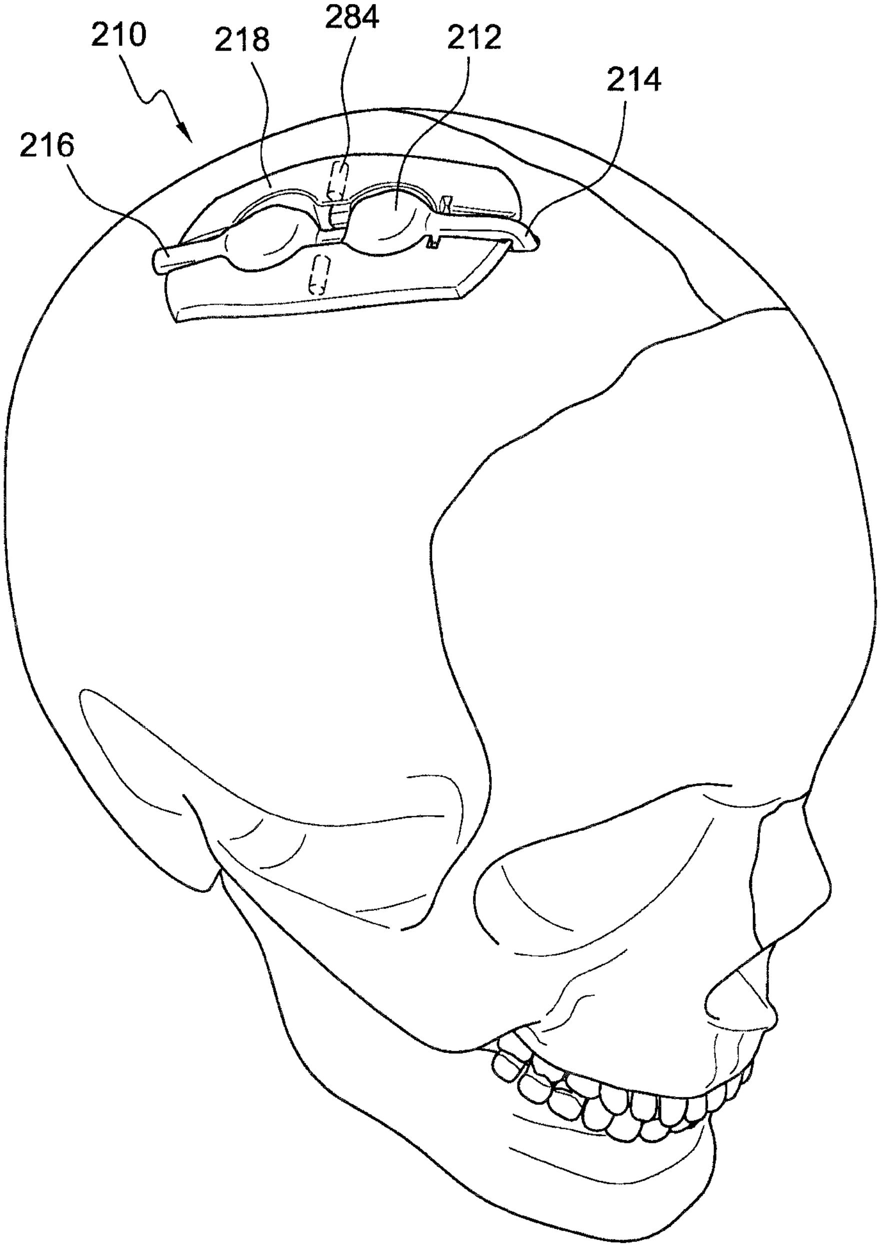
Figure 22:
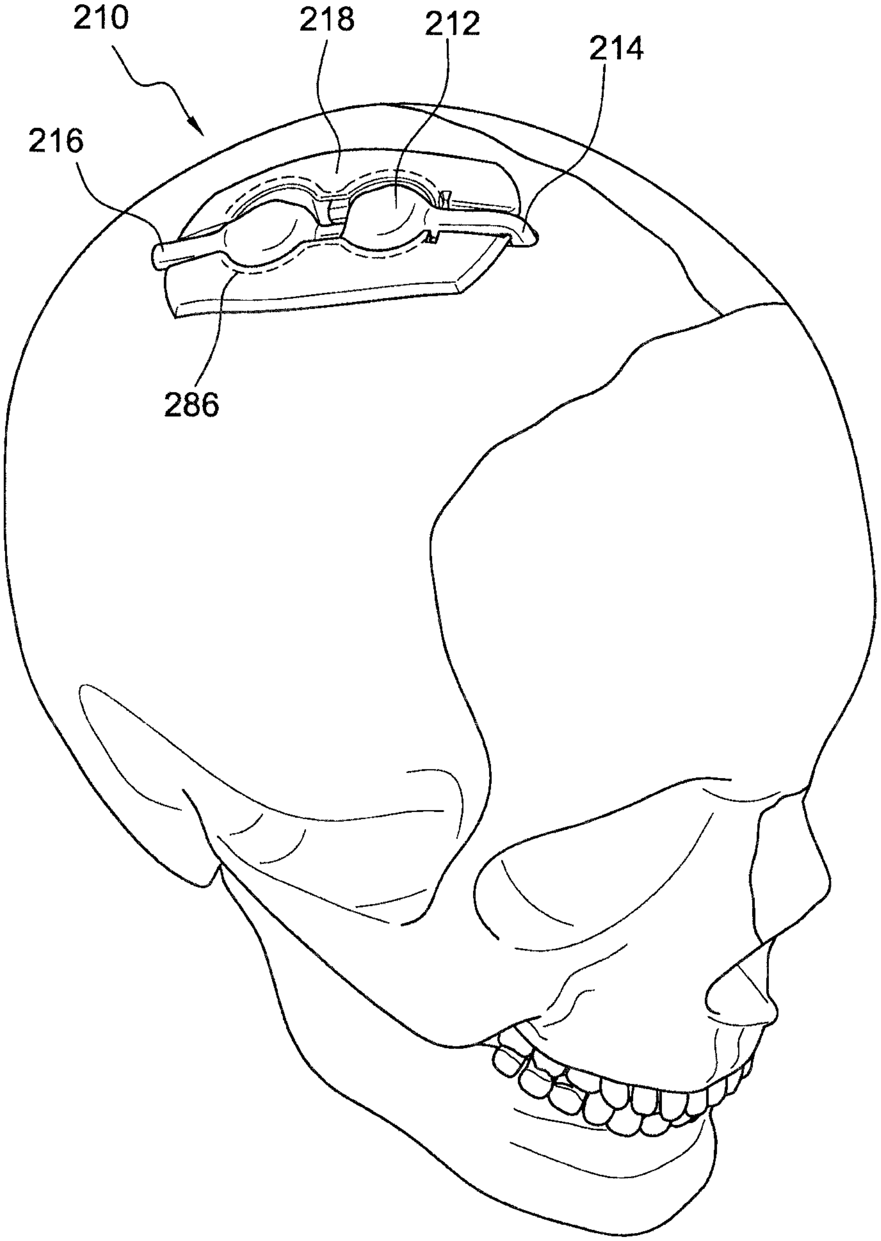

In accordance with the embodiment disclosed with reference to FIG. 19, physical bumps 280*a-d* are provided on the housing 218 of the shunt plug 210. While four bumps are shown in accordance with a disclosed embodiment, it is appreciated the number and location of the bumps may be varied to suit specific needs. In accordance with the embodiment disclosed with reference to FIG. 20, magnets or ferromagnetic properties 282 are integrated into the housing 218. The magnets or ferromagnetic properties 282 are oriented in the housing 218 to allow an external magnet to be employed in triangulating a particular location upon the shunt plug 210. In accordance with the embodiment disclosed with reference to FIG. 21, an RFID (radio-frequency identification) device 284 is embedded in the housing 218 of the shunt plug 210 with the ability to identify a point on the shunt plug 210. In accordance with the embodiment disclosed with reference to FIG. 22, radiographic and/or acoustic properties 286 are integrated into the housing 218 that allow specific points of the shunt plug 210 to be seen by imaging modalities (CT, MRI, X-ray, Ultrasound, etc . . . ). While the various identification devices described above are integrated into the housing, it is appreciated they might also be integrated into the shunt valve without departing from the spirit of the present invention.

Figure 23:
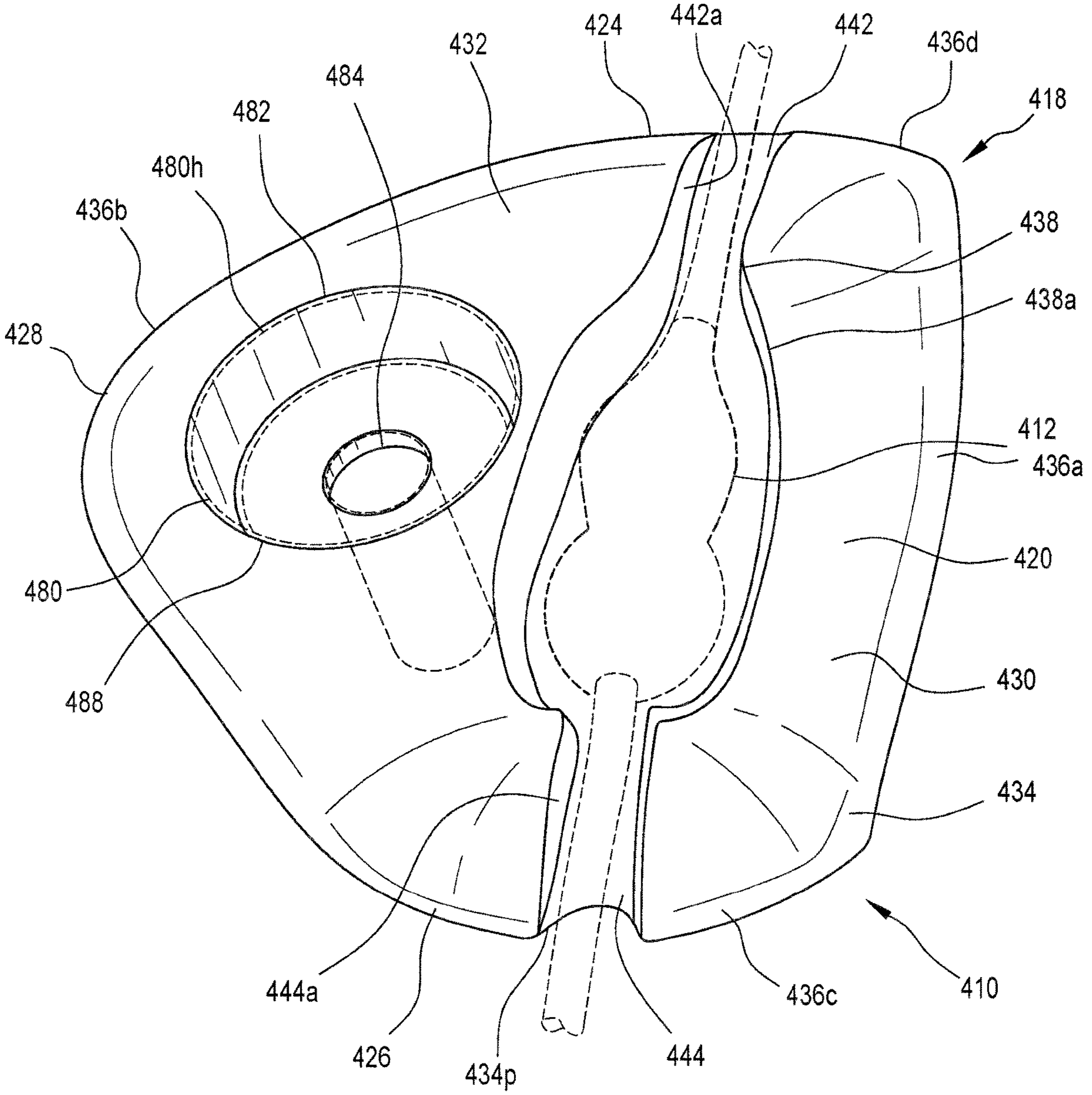
FIGS. 23 and 24 are top and bottom perspective views showing a cerebral spinal fluid shunt plug in accordance with an alternate embodiment.
Figure 24:
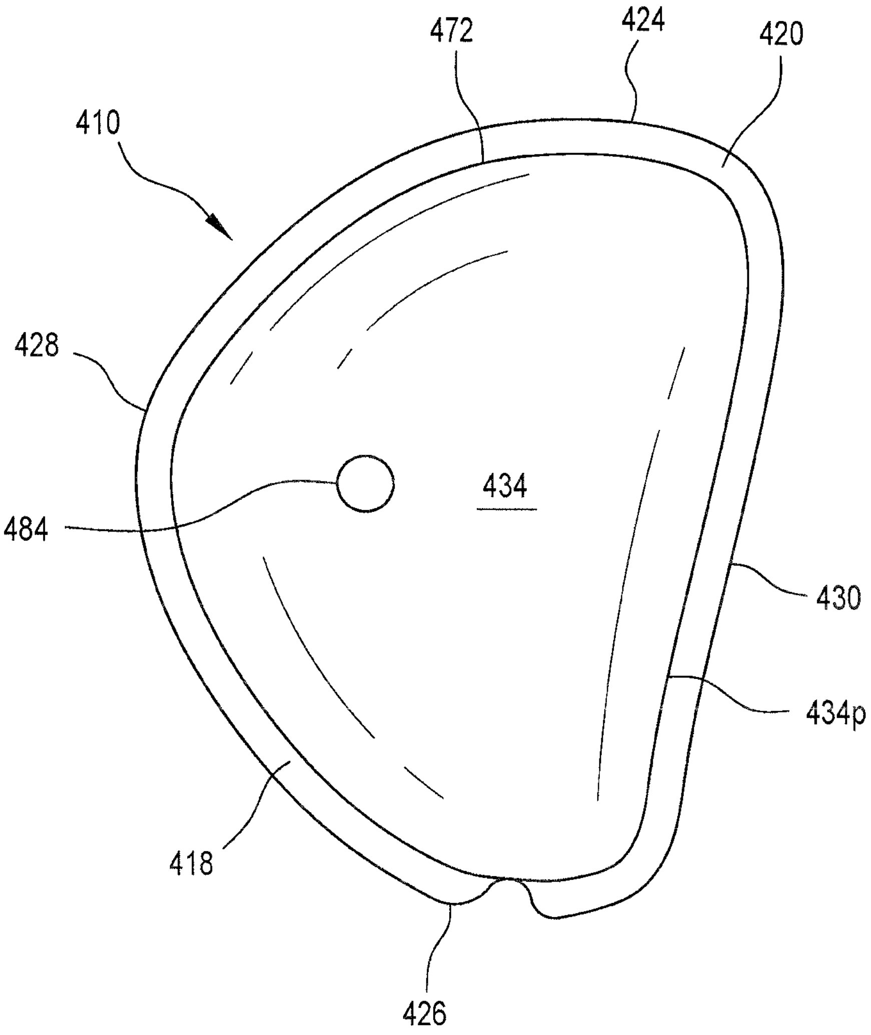
Figure 25:
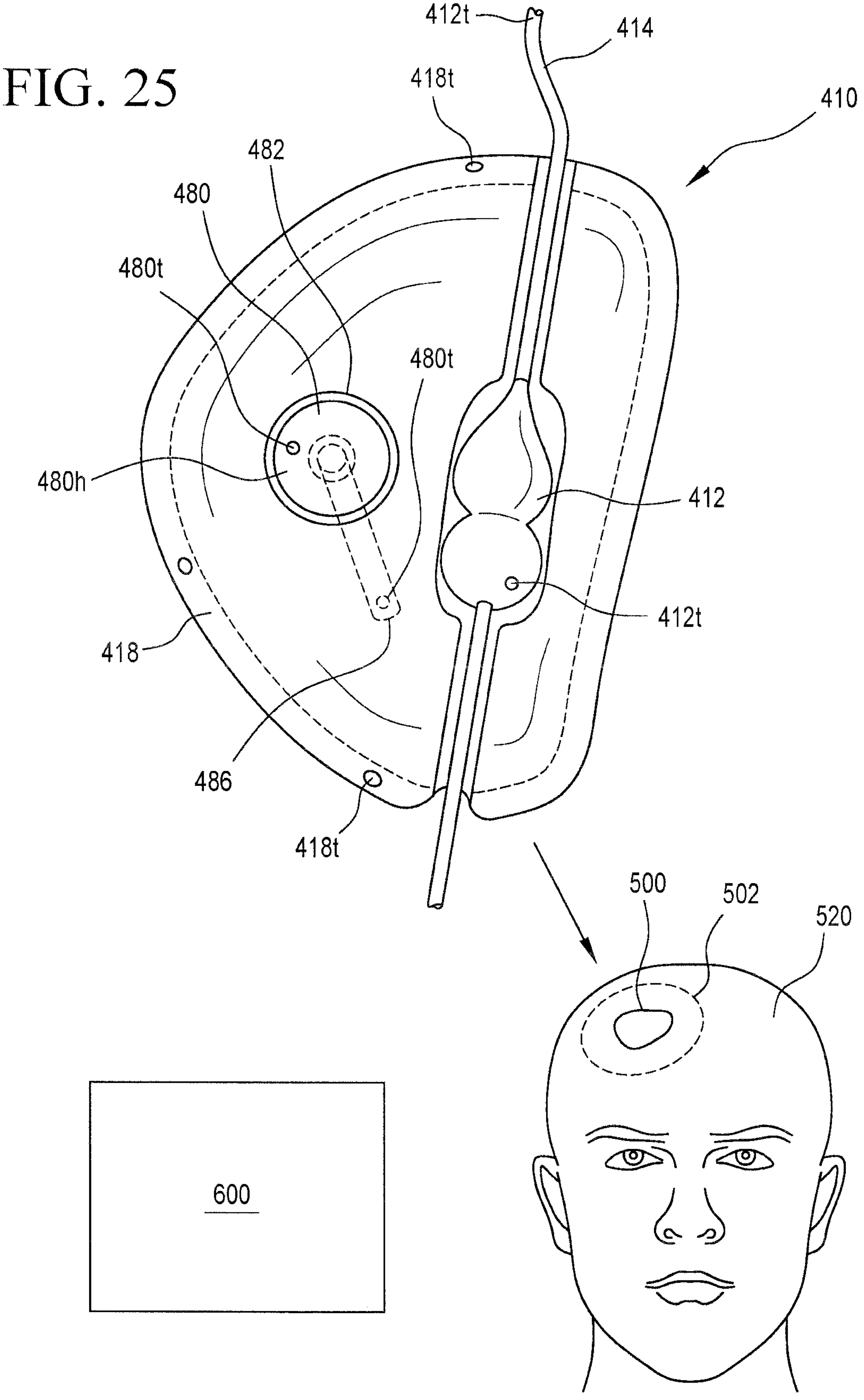
FIG. 25 is a schematic showing the process of implanting the cerebral spinal fluid shunt plug shown in FIGS. 23 and 24.

Referring to FIGS. 23 to 25, yet another embodiment of the present cerebral spinal fluid shunt plug 410 is disclosed. As with the prior embodiments, the shunt plug 410 is shaped and dimensioned for positioning within a physician formed cranial hole 500 and is further shaped and dimensioned for housing a shunt valve 412 in a reliable and secure manner so that a ventricular catheter 414 and peritoneal catheter 416 may be positioned without fear that the shunt valve 412 might move and/or the catheters 414, 416 might become disengaged from their desired locations. Still further, this embodiment is shaped and dimensioned for integration of a wireless intracranial monitoring device 480 with the shunt plug 410.

The shunt plug 410 includes a shunt plug housing 418 composed of a bottom first housing member 420. In accordance with the disclosed embodiments, the shunt valve 412 and the wireless intracranial monitoring device 480 are placed within the shunt plug housing 418, so as to create the shunt plug 410 of the present invention, at the time of surgery.

The shunt plug housing 418 is substantially triangular shaped (with curved and extended corners, as well as arcuate walls) and includes a first end 424, a second end 426, a short first lateral side 428, and a long second lateral side 430. However, and as with the prior embodiments, it is appreciated various shapes may be employed within the spirit of the present invention and the shape of the shunt plug housing may be varied without departing from the spirit of the present invention.

The shunt plug housing 418 also includes an upper surface 432, a lower surface 434, and continuous side walls 436*a-d* extending between the upper surface 432 and the lower surface 434, as well as about the periphery of the shunt plug housing 418. As will be appreciated based upon the following disclosure, and as with the embodiment of FIGS. 9-18, the lower surface 434 is provided with a projection 434*p* that ultimately fits within the cranial hole 500 to assist in holding the shunt plug 410 in position after installation. With this in mind, the projection 434*p* is shaped to fit within the cranial hole 500 as shown in FIG. 25.

While a particular shape of the shunt plug housing 418 in accordance with the disclosed embodiment is disclosed herein for the purpose of explaining the present invention, it is appreciated various shapes may be employed within the spirit of the present invention. As such, the shape of the shunt plug and the mechanism for the creation of the cranial hole are intimately related and may be varied based upon various needs and requirements. For example, and in contrast with the embodiments described above with reference to FIGS. 1 to 22, the shunt plug housing includes a substantially triangular shape.

A shunt valve recess 438 is formed within the upper surface 432 of the shunt plug housing 418. The shunt valve recess 438 is in communication with the exterior of the shunt plug housing 418 via access passageways 442, 444 extending from the exterior surface of the shunt plug housing 418 to the shunt valve recess 438. As will be explained below in greater detail, these access holes (or passageways) 442, 444 allow for connection of the ventricular catheter 414 and the peritoneal catheter 416 with the shunt valve 412 housed within the shunt valve recess 438 of the shunt plug housing 418. The access passageways 442, 444 are defined by recessed surfaces formed along the upper surface 432 of the shunt plug housing 418. Depending upon the shape of the shunt plug housing 418 and the shunt valve 412 to be positioned therein, the position of the access holes (or passageways) 442, 444 may be varied to optimize the ultimate positioning of the peritoneal catheter 416 and the ventricular catheter 414.

As discussed above, the shunt valve recess 438 in which the shunt valve 412 is positioned, as well as the access holes 442, 444 for the passage of the ventricular and peritoneal catheters 414, 416, are formed within the shunt plug housing 418. The shunt valve recess 438 and access holes 442, 444 are defined by recessed surfaces 438*a*, 442*a*, 444*a* formed along the upper surface 432 of the shunt plug housing 418. In particular, the recessed surface 438*a* defining the shunt valve recess 438 is formed along the upper surface 432 of the shunt plug housing 418; the recessed surface 442*a* defining the first access hole (or passageway) 442 is formed along the upper surface 432 adjacent the first end 424; and the recessed surfaces 444*a* defining the second access hole (or passageway) 444 are formed along the side wall 464*a* of the shunt plug housing 418 at the second end 426 thereof.

As briefly discussed above, the shunt valve recess 438 defined within the shunt plug housing 418 is shaped and dimensioned for placement of the shunt valve 412 therein. As those skilled in the art will appreciate, and as explained above in conjunction with the prior embodiment, a variety of shunt valves are known in the art and the present shunt plug housing 418 may be adapted to accommodate a variety of these shunt valves. The present invention may also be used in conjunction with the Rickam reservoir and other similar reservoirs used in cerebral spinal fluid management. In accordance with a preferred embodiment, the shunt plug housing 418 should have a surface area along its upper surface 432 of at least five $cm^2$ so as to accommodate various shunt valves and to provide the necessary space for placement of the shunt valve 412 within the shunt valve recess 438 defined within the shunt plug housing 418.

As will be explained below in detail, once the shunt valve 412 is positioned within the shunt valve recess 438 of the shunt plug housing 418 the shunt plug 410 of the present invention may be utilized for the purpose of performing a cerebral spinal fluid shunt procedure.

In addition to the shunt valve recess 438 for the shunt valve 412 as discussed above, the shunt plug housing 418 of this embodiment further includes an intracranial monitoring device recess 482 formed within the upper surface 432 of the shunt plug housing 418 adjacent to the short first lateral side 428. The intracranial monitoring device recess 482 is shaped and dimensioned for positioning of an intracranial monitoring device 480, in particular, the head 480*h* of the intracranial monitoring device 480, therein. As such, and as will be appreciated based upon the following disclosure, the intracranial monitoring device recess 482 is provided with a central access hole 484 extending from the intracranial monitoring device recess 482 to the lower surface 434 of the shunt plug housing 418. The central access hole 484 is shaped and dimensioned for the passage of the probe 486 of the wireless intracranial monitoring device 480 therethrough and to a desired position within the brain.

The intracranial monitoring device recess 482 in which the wireless intracranial monitoring device 480 is positioned, as well as the central access hole 484 for the passage of the probe 486, is formed within the shunt plug housing 418. The intracranial monitoring device recess 482 is defined by recessed surfaces 488 formed along the upper surface 432 of the shunt plug housing 418. In particular, the recessed surface 488 defining the intracranial monitoring device recess 482 is formed along the upper surface 432 of the shunt plug housing 418.

As briefly discussed above, the intracranial monitoring device recess 482 defined within the shunt plug housing 418 is shaped and dimensioned for placement of the wireless intracranial monitoring device 480 therein. As those skilled in the art will appreciate, and as explained above in conjunction with the prior embodiment, a variety of wireless intracranial monitoring devices are known in the art and the present shunt plug housing 418 may be adapted to accommodate a variety of these wireless intracranial monitoring device 480. However, and in accordance with a preferred embodiment of the present invention, the wireless intracranial monitoring device 480 is one or a combination of the wireless intracranial pressure monitoring devices disclosed in U.S. Pat. Nos. 8,337,413 and 9,339,189 and U.S. Patent Application Publication Nos. 2006/0025704, 2008/0161659, 2008/0262319, 2011/0009716, 2013/0123660, and 2014/0210637, all of which are incorporated herein by reference. In accordance with this embodiment, the shunt plug housing 418 should have a surface area along its upper surface 432 sufficient to accommodate various shunt valves and wireless intracranial monitoring devices.

The inclusion of the wireless intracranial monitoring device 480 with the shunt plug 410 of the present invention results in a reduction in the pressure generated by mounting implantable devices on the scalp and allows for measurement of the cerebral spinal fluid manage by the shunt valve 412 itself.

Further functionality may be achieved by using a wireless intracranial monitoring device offering multiple sensing capabilities (multimodal), for example, as disclosed in U.S. Patent Application Publication No. 2018/0325386, entitled "MULTIPLE IMPLANTABLE SENSOR PROBE," published Nov. 15, 2018, which is incorporated herein by reference.

Once the shunt valve 412 and the wireless intracranial monitoring device 480 are positioned within the shunt valve recess 438 of the shunt plug housing 418 the shunt plug 410 of the present invention may be utilized for the purpose of performing a cerebral spinal fluid shunt procedure as explained above.

With the inclusion of a wireless intracranial monitoring device 480 with the shunt plug 410 of the present invention, positioning of the shunt plug 410 becomes critical. As such, the installation procedure is modified as described below.

Referring to FIG. 25, the procedure is first initiated by making the required incision for passage of the peritoneal catheter 416. Thereafter, a cranial incision is made and the cranial hole 500 in the skull 520 is created utilizing a template 502 (shown in broken lines). In accordance with a preferred embodiment, and considering the triangular shape of the cranial hole 500, burr holes are formed at the respective ends of the template 502, and the remainder of the skull 520 is cut away along the lines as defined by the template 502. As with the prior embodiment, it is appreciated the cranial hole may be made using any method acceptable to those skilled in the art. Given the matching shape of the cranial hole 500 and the shunt plug 410, the shunt plug 410 will fit snugly within the cranial hole 500 thereby minimizing potential movement after completion of the procedure.

With the cranial hole 500 completed, the ventricular catheter 414 is positioned within the ventricle and the peritoneal catheter 416 is positioned with the body as using well know medical procedures. Thereafter, the shunt plug housing 418 is positioned within the cranial hole 500 with the upper surface 432 facing upwardly, and the ventricular catheter 414 is cut to an appropriate length. The ends of the peritoneal catheter 416 and the ventricular catheter 414 adjacent the shunt plug 410 are then secured to the shunt valve 412 and the shunt valve 412 is positioned within the shunt plug housing 418. In particular, the shunt plug 10 is mounted within the cranial hole 500 such that the upper surface 432 is substantially flush with the outer surface of the skull 520 and the projection 434*p* along the lower surface 434 is positioned within the cranial hole 500. As such, portions along the periphery of the shunt plug housing 418 overlie the skull 520, and screws may be passed therethrough to facilitate secure attachment of the shunt plug 410 to the skull. It is, however, appreciated the exact positioning of the shunt plug will vary based upon specific anatomical characteristics of the patient. Once the shunt plug 410 is properly positioned and secured in place using known techniques, the wireless intracranial monitoring device 480 is positioned within the intracranial monitoring device recess 482 with the probe 486 extending into the brain.

As those skilled in the art will appreciate, proper positioning of the probe 486 of the intracranial monitoring device 480 and the ventricular catheter 414 of the shunt valve 412 are critical. The orientation of the wireless intracranial monitoring device 480, for example, the probe 486 of the intracranial monitoring devices 480, relative to ventricular catheter 414 of the shunt valve 412 is critical to understand and appreciate so as to avoid eloquent structures on the cortex of the brain; such as the trajectory between Kocher's point and the ventricles or previously necrosed brain damage in a traumatic injury or due to high intracranial pressure. Furthermore, by identifying the relative positions of the wireless intracranial monitoring device 480 and the shunt valve 412 to the cortex, the relationship of the shunt valve 412 and wireless intracranial monitoring device 480 relative to a target within the brain is surmised and eloquent structures of the brain are avoided. For example, and through the use of the present shunt plug 410 in conjunction with various computer based surgical guidance systems 600 as discussed below, it is possible for surgeons to fully appreciate the relationship of the intracranial monitoring device 480, the shunt valve 412, and/or the ventricular catheter 418 in relation to the shunt plug 410 and, therefore, the cortex. This enables the surgeon to place the intracranial monitoring device 480, the shunt valve 412, and/or the ventricular catheter 418 in a manner that minimizes the potential for cortical damage.

In practice, and prior to initiating the surgical procedure, virtual images of the shunt plug 410, including both the shunt valve 412 and the intracranial monitoring device 480, are generated. Virtual images of the patient, including the approximate location of the shunt plug 410 are also generated. Upon initiation of the surgical procedure movement of the actual shunt plug 410, including the shunt valve 412, shunt plug housing 418, and the intracranial monitoring device 480, relative to the patient is monitored in real-time. This is achieved by the integration of tracking devices 412*t*, 418*t*, 480*t* into or onto the respective shunt valve 412, shunt plug housing 418, and the intracranial monitoring device 480. Additional tracking devices may be applied to the patient in a manner known to those skilled in the art. It should be appreciated that the tracking devices 412*t*, 418*t*, 480*t* may take a variety of forms so long as the computer-based guidance system 600 is capable of identifying the real-time movement of the various components of the shunt plug 410 being tracked. For example, the tracking devices may take the form of external tracking devices attached to the shunt plug, tracking devices integrated into the shunt plug, or existing structures of the shunt plug that are readily identifiable via the sensing structure of the computer-based guidance system 600. Sensing may be achieved via various known techniques, including, but not limited to, infrared, electromagnetic, optical, etc. sensing techniques.

With this information and using a computer based surgical guidance system 600, the shunt plug 410 is properly positioned within the patient. Once the shunt valve 412 and the wireless intracranial monitoring device 480 are properly positioned, they may be actuated utilizing well known procedures, and the procedure is completed in accordance with known medical procedures.

Figure 26:
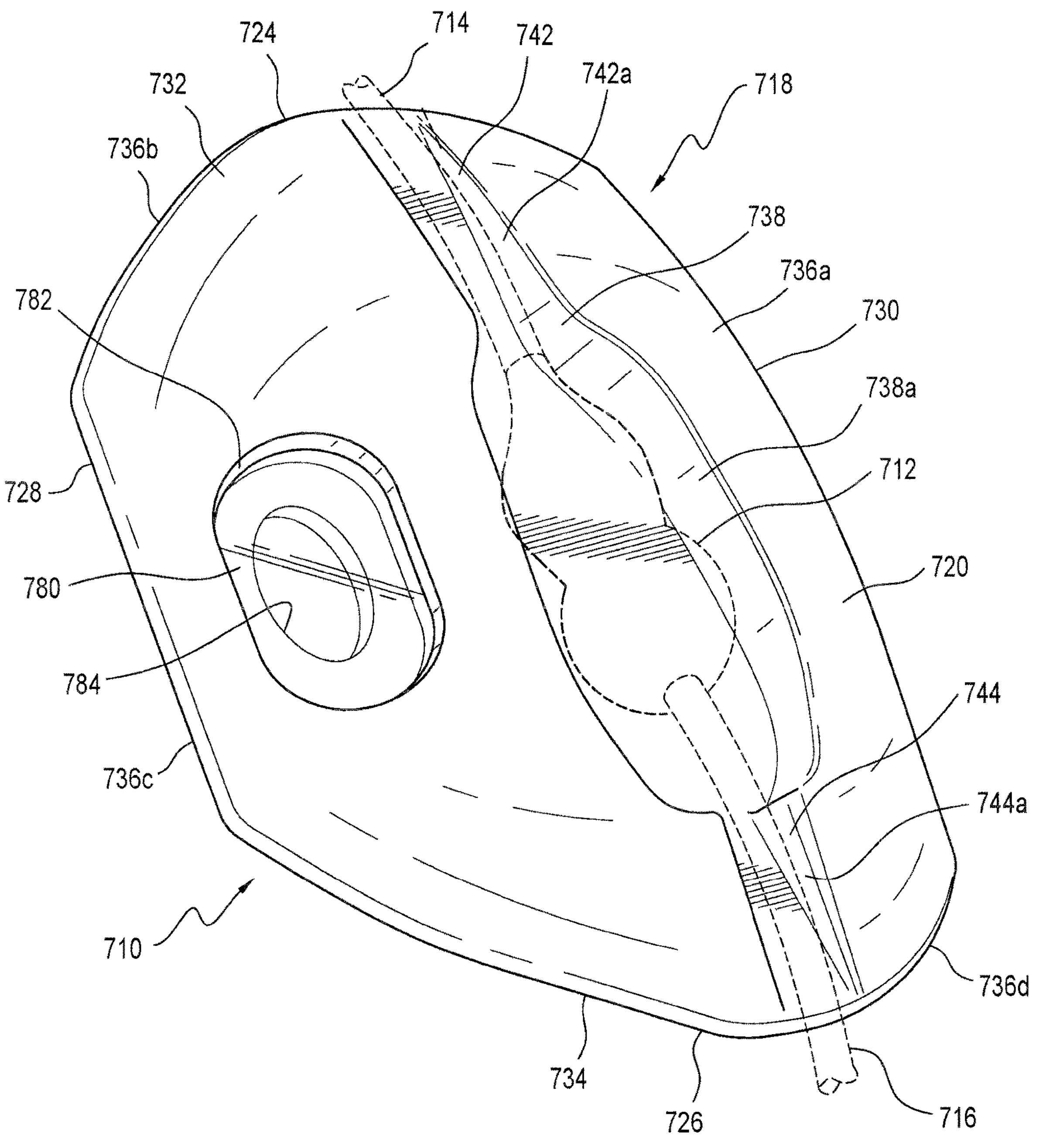
FIGS. 26 and 27 are perspective views of a cerebral spinal fluid shunt plug in accordance with an alternate embodiment with the lucent disk shown and not shown, respectively, and also showing that the lucent disk and window recess may be formed in various shapes.
Figure 27:
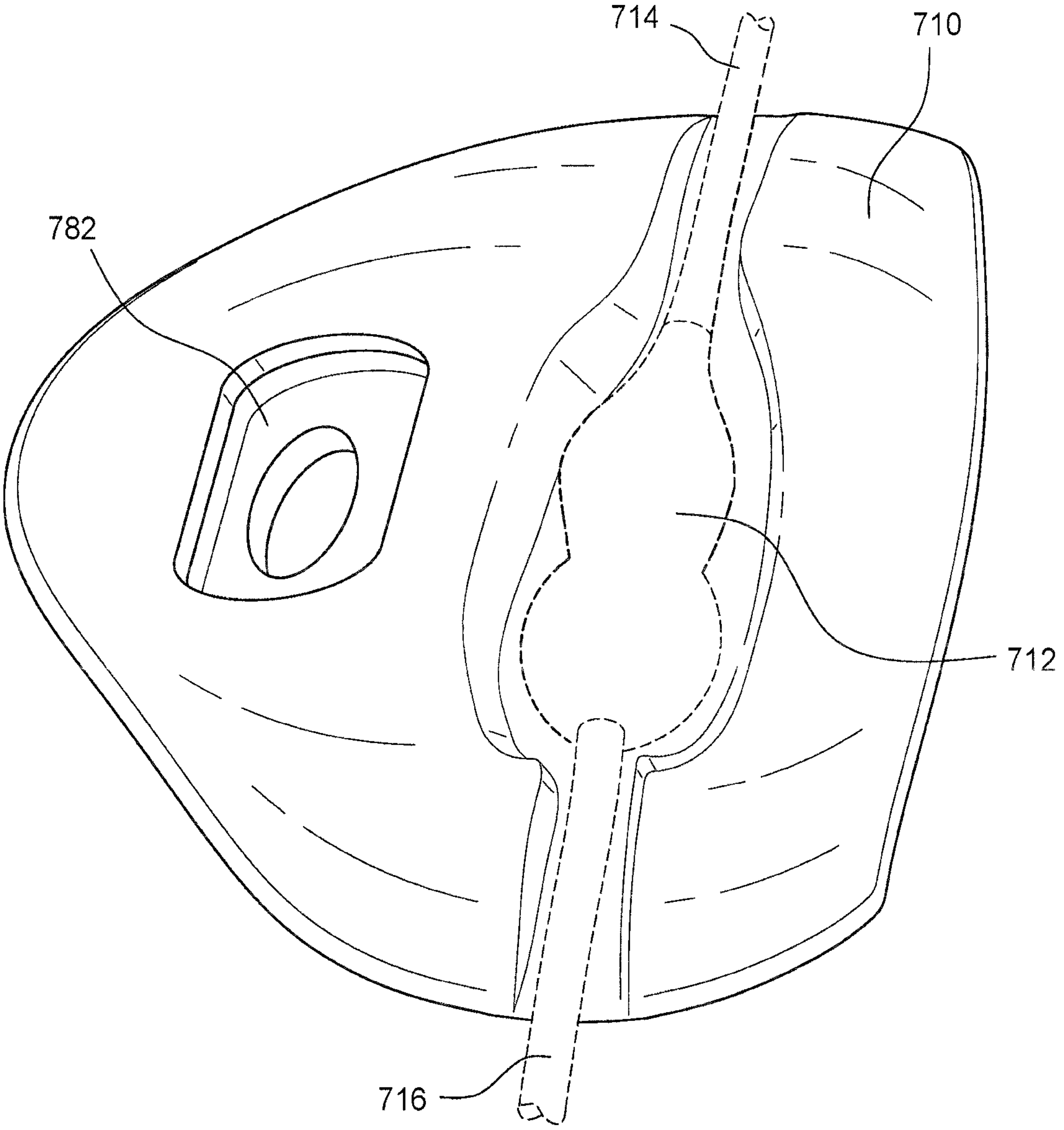
Figure 28:
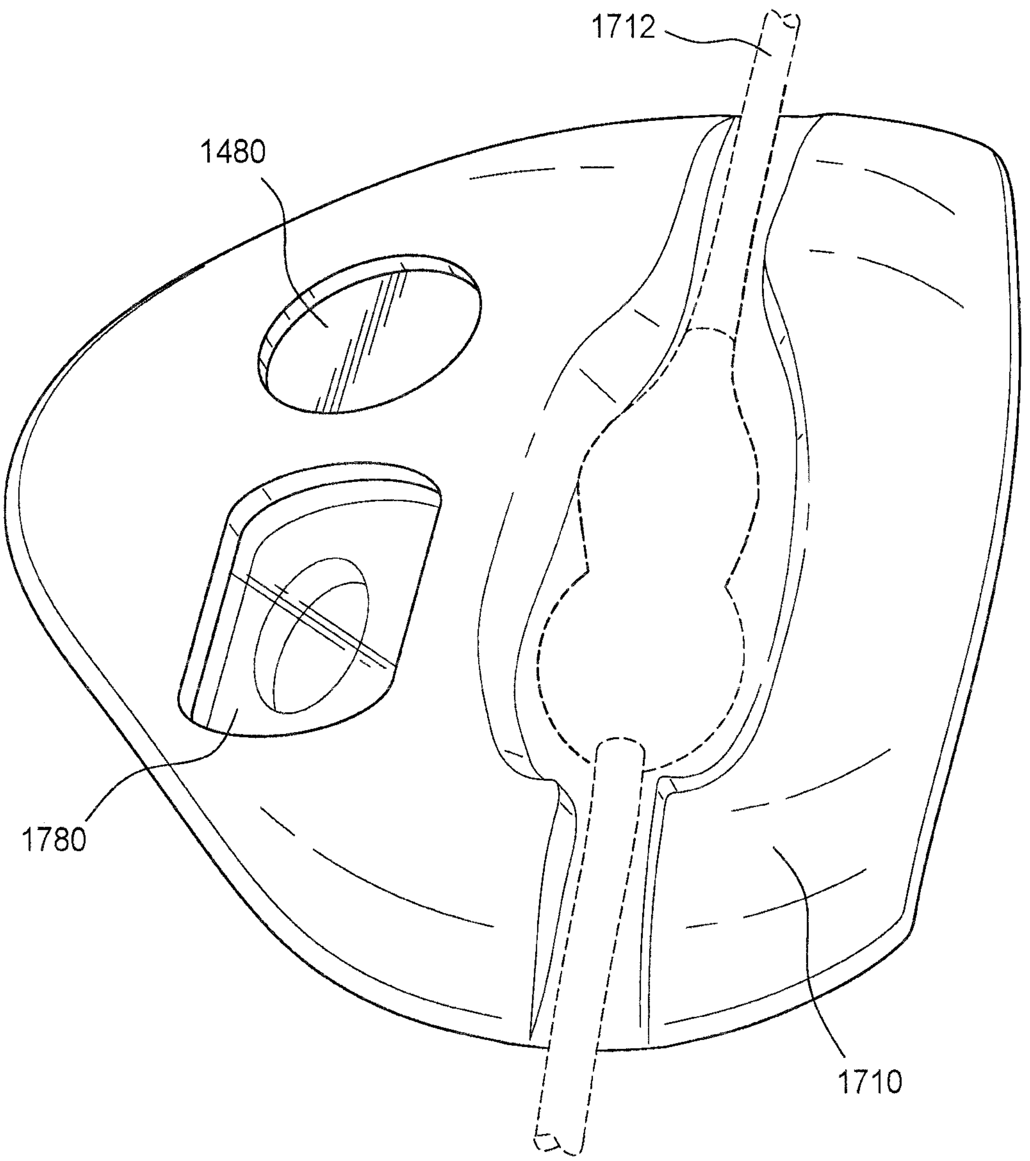
FIG. 28 is a perspective view of a cerebral spinal fluid shunt plug in accordance with an alternate embodiment.

Referring to FIGS. 26 and 27, yet another embodiment of the present cerebral spinal fluid shunt plug 710 is disclosed. As with the prior embodiments, the shunt plug 710 is shaped and dimensioned for positioning within a physician formed cranial hole and is further shaped and dimensioned for housing a shunt valve 712 in a reliable and secure manner so that a ventricular catheter 714 and peritoneal catheter 716 may be positioned without fear that the shunt valve 712 might move and/or the catheters 714, 716 might become disengaged from their desired locations. Still further, this embodiment is shaped and dimensioned for integration of a window in the form of a lucent disk 780 with the shunt plug 710. Given the similarity between the embodiment disclosed with reference to FIGS. 23 to 25 and the embodiment disclosed with reference to FIGS. 26 and 27, it is appreciated one shunt plug housing 718 may be used in conjunction with either the wireless intracranial monitoring device 480 of the embodiment disclosed with reference to FIGS. 23 to 25 or the lucent disk 780 of the embodiment disclosed with reference to FIGS. 26 and 27. Further still, and with reference to FIG. 28, an embodiment combining the lucent disk 1780 and the wireless intracranial monitoring device 1480 for use with a shunt valve 1712 is disclosed.

The shunt plug 710 includes a shunt plug housing 718 composed of a bottom first housing member 720. In accordance with the disclosed embodiments, the shunt valve 712 and the lucent disk 780 are placed within the shunt plug housing 718, so as to create the shunt plug 710 of the present invention, at the time of surgery.

The shunt plug housing 718 is substantially triangular shaped (with curved and extended corners, as well as arcuate walls) and includes a first end 724, a second end 726, a short first lateral side 728, and a long second lateral side 730. However, and as with the prior embodiments, it is appreciated various shapes may be employed within the spirit of the present invention and the shape of the shunt plug housing may be varied without departing from the spirit of the present invention.

The shunt plug housing 718 also includes an upper surface 732, a lower surface 734, and continuous side walls 736*a-d* extending between the upper surface 732 and the lower surface 734, as well as about the periphery of the shunt plug housing 718. As will be appreciated based upon the following disclosure, and as with the embodiment of FIGS. 9-18, the lower surface (not shown) is provided with a projection (not shown) that ultimately fits within the cranial hole to assist in holding the shunt plug 710 in position after installation. With this in mind, the projection is shaped to fit within the cranial hole 500 as shown in FIG. 25.

While a particular shape of the shunt plug housing 718 in accordance with the disclosed embodiment is disclosed herein for the purpose of explaining the present invention, it is appreciated various shapes may be employed within the spirit of the present invention. As such, the shape of the shunt plug and the mechanism for the creation of the cranial hole are intimately related and may be varied based upon various needs and requirements. For example, and in contrast with the embodiments described above with reference to FIGS. 1 to 22, the shunt plug housing includes a substantially triangular shape.

A shunt valve recess 738 is formed within the upper surface 732 of the shunt plug housing 718. The shunt valve recess 738 is in communication with the exterior of the shunt plug housing 718 via access passageways 742, 744 extending from the exterior surface of the shunt plug housing 718 to the shunt valve recess 738. As will be explained below in greater detail, these access holes (or passageways) 742, 744 allow for connection of the ventricular catheter 714 and the peritoneal catheter 716 with the shunt valve 712 housed within the shunt valve recess 738 of the shunt plug housing 718. The access passageways 742, 744 are defined by recessed surfaces formed along the upper surface 732 of the shunt plug housing 718. Depending upon the shape of the shunt plug housing 718 and the shunt valve 712 to be positioned therein, the position of the access holes (or passageways) 742, 744 may be varied to optimize the ultimate positioning of the peritoneal catheter 716 and the ventricular catheter 714.

As discussed above, the shunt valve recess 738 in which the shunt valve 712 is positioned, as well as the access holes 742, 744 for the passage of the ventricular and peritoneal catheters 714, 716, are formed within the shunt plug housing 718. The shunt valve recess 738 and access holes 742, 744 are defined by recessed surfaces **738*a*, 742*a*, 744*a* formed along the upper surface 732 of the shunt plug housing 718. In particular, the recessed surface 738*a* defining the shunt valve recess 738 is formed along the upper surface 732 of the shunt plug housing 718; the recessed surface 742*a* defining the first access hole (or passageway) 742 is formed along the upper surface 732 adjacent the first end 724; and the recessed surfaces 744*a* defining the second access hole (or passageway) 744 are formed along the side wall 736*a* of the shunt plug housing 718 at the second end 726** thereof.

As briefly discussed above, the shunt valve recess 738 defined within the shunt plug housing 718 is shaped and dimensioned for placement of the shunt valve 712 therein. As those skilled in the art will appreciate, and as explained above in conjunction with the prior embodiment, a variety of shunt valves are known in the art and the present shunt plug housing 718 may be adapted to accommodate a variety of these shunt valves. The present invention may also be used in conjunction with the Rickam reservoir and other similar reservoirs used in cerebral spinal fluid management. In accordance with a preferred embodiment, the shunt plug housing 718 should have a surface area along its upper surface 732 of at least five $cm^2$ so as to accommodate various shunt valves and to provide the necessary space for placement of the shunt valve 712 within the shunt valve recess 738 defined within the shunt plug housing 718.

As will be explained below in detail, once the shunt valve 712 is positioned within the shunt valve recess 738 of the shunt plug housing 718 the shunt plug 710 of the present invention may be utilized for the purpose of performing a cerebral spinal fluid shunt procedure.

In addition to the shunt valve recess 738 for the shunt valve 712 as discussed above, the shunt plug housing 718 of this embodiment further includes a window recess 782 formed within the upper surface 732 of the shunt plug housing 718 adjacent to the short first lateral side 728. The window recess 782 is shaped and dimensioned for positioning of a lucent disk 780. As such, and as will be appreciated based upon the following disclosure, the window recess 782 is provided with a central access hole 784 extending from the window recess 782 to the lower surface 734 of the shunt plug housing 718. The central access hole 784 is shaped and dimensioned for the passage of light, sound, and/or radio waves therethrough so as to access the brain for imaging and treatment.

The window recess 782 in which the lucent disk 780 is positioned, as well as the central access hole 784, is formed within the shunt plug housing 718. The window recess 782 is defined by recessed surfaces 788 formed along the upper surface 732 of the shunt plug housing 718. In particular, the recessed surface 788 defining the window recess 782 is formed along the upper surface 732 of the shunt plug housing 718.

Figure 29:
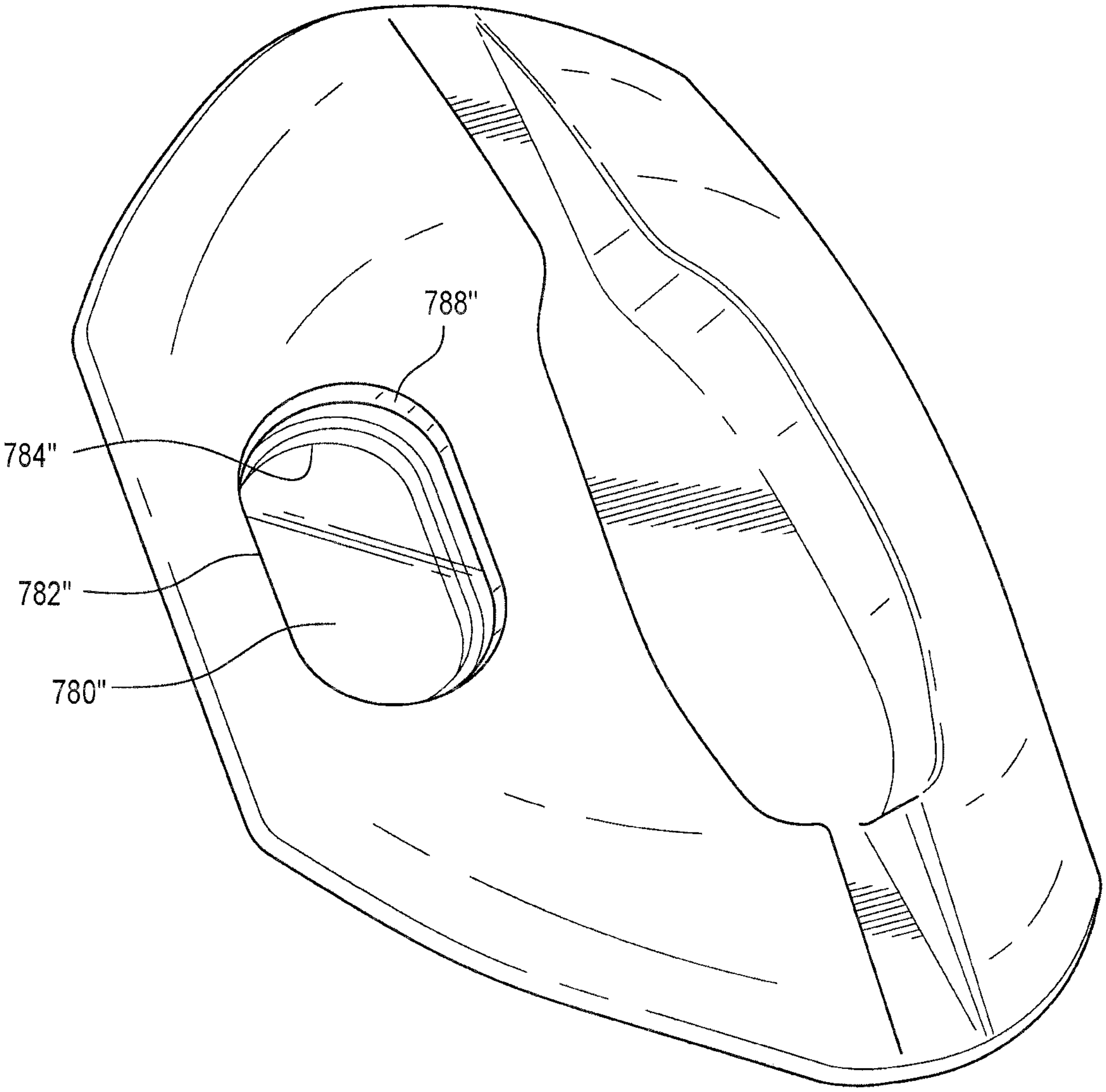
FIG. 29 is a perspective view of a cerebral spinal fluid shunt plug in accordance with an alternate embodiment.

While the embodiment described considers a situation wherein the shunt plug housing 718 may be used in conjunction with either the wireless intracranial monitoring device 480 of the embodiment disclosed with reference to FIGS. 23 to 25 or the lucent disk 780 of the embodiment disclosed with reference to FIGS. 26 and 27, the shunt plug housing may be specifically designed for use with only the lucent disk. Considering such an embodiment, and with reference to FIG. 29, the central access hole 784" would be substantially enlarged such that the recessed surface 788" positioned about the central access hole 784" is made relatively small and is constructed to function as a ledge supporting the bottom surface of the lucent disk 780" when it is positioned within the window recess 782". By expanding the central access hole 784", unattenuated passage of light, sound, radio, and other waves will be optimized.

As briefly discussed above, the window recess 782 defined within the shunt plug housing 718 is shaped and dimensioned for placement of the lucent disk 780 therein. In accordance with a preferred embodiment of the present invention, the lucent disk 780 is optically transparent, optically translucent to all light waves, sonolucent (that is, allowing passage of ultrasonic waves without production of echoes that are due to reflection of some of the waves), and/or radiolucent (that is, allowing passage of radio waves without production of echoes that are due to reflection of some of the waves). Further still, and in accordance with a disclosed embodiment, the lucent disk is made of polymethyl methacrylate (PMMA).

Through the provision of a lucent disk, a variety of options are available to medical practitioners wishing to provide the best treatment options to their patients. For example, lucent disk may be manufactured in a manner allowing for the transmission of ultrasonic waves as described in U.S. Pat. No. 9,044,195, entitled "IMPLANTABLE SONIC WINDOW," ('195 Patent) which is incorporated herein by reference. As explained in the '195 Patent, a strong, porous sonically translucent material through which ultrasonic waves can pass for purposes of imaging the brain is employed, wherein the material is a polymeric material, such as polyethylene, polystyrene, acrylic, or poly(methyl methacrylate) (PMMA). In addition, U.S. Pat. No. 9,535,192, entitled "METHOD OF MAKING WAVEGUIDE-LIKE STRUCTURES," ('192 Publication) and U.S. Patent Application Publication No. 2017/0156596, entitled "CRANIAL IMPLANTS FOR LASER IMAGING AND THERAPY," ('596 Publication) both of which are incorporated herein by reference, making waveguide-like structures within optically transparent materials using femtosecond laser pulses wherein the optically transparent materials are expressly used in the manufacture of cranial implants. The '596 publication explains the use of optically transparent cranial implants and procedures using the implants for the delivery of laser light into shallow and/or deep brain tissue. The administration of the laser light can be used on demand, thus allowing real-time and highly precise visualization and treatment of various pathologies. Further still, Tobias et al. describe an ultrasound window to perform scanned, focused ultrasound hyperthermia treatments of brain tumors. Tobias et al., "ULTRASOUND WINDOW TO PERFORM SCANNED, FOCUSED ULTRASOUND HYPERTHERMIA TREATMENTS OF BRAIN TUMORS," Med. Phys. 14(2), March/April 1987, 228-234, which is incorporated herein by reference. Tobias et al. tested various materials to determine which material would best serve as an acoustical window in the skull and ultimately determined polyethylene transmitted a larger percentage of power than other plastics and would likely function well as an ultrasonic window. Further still, Fuller et al., "REAL TIME IMAGING WITH THE SONIC WINDOW: A POCKET-SIZED, C-SCAN, MEDICAL ULTRASOUND DEVICE," IEEE International Ultrasonics Symposium Proceedings, 2009, 196-199, which is incorporated herein by reference, provides further information regarding sonic windows.

Radiolucency as applied to the present invention allows a clinician to see the anatomy beneath the lucent disk 780 without "scatter" or interfering artifacts from the implant for diagnosis and follow-up. By another definition of radiolucency, radio waves are able to transmit easily through the lucent disk 780, for example, via Bluetooth or other radiofrequency transmission method; which can serve many purposes including, but not limited to, data management and controller telemetry. The provision of radiolucency also allows for the integration of markings (as discussed below) made with radiographic materials, for example, barium sulfate, to be visible in contrast to the remainder of the craniofacial implant to allow for unique device identifiers or unique patient information to be visible on post-operative scans.

Considering the provision of optical lucency in the lucent disk 780, the ability to optically transmit through the lucent disk 780 allows for: visualization of anatomy distal to the lucent disk 780, the potential of higher bandwidth optical links (similar to radio transmission) between proximal adjunct devices, light to be emitted through the lucent disk 780 to adjacent anatomy which could aid in optogenetics, and imaging/therapeutic modalities that rely on light like optical coherence tomography from within the implant. Of note, this was shown to be true on a postoperative (day 5) cranioplasty patient with the clear implant. Belzberg M, Ben Shalom N, Yuhanna E, Manbachi A, Tekes A, Huang J, Brem H, Gordon C, "Sonolucent Cranial Implants: Cadaveric study and Clinical Findings Supporting Diagnostic and Therapeutic Trans-Cranioplasty Ultrasound," J Craniofac Surg. (July/August 2019—Volume 30—Issue 5—p 1456-1461).

With the inclusion of a lucent disk 780 with the shunt plug 710 of the present invention, positioning of the shunt plug 710 becomes critical. As such, the installation procedure is as described below.

The procedure is first initiated by making the required incision for passage of the peritoneal catheter 716. Thereafter, a cranial incisions made and the cranial hole in the skull is created utilizing a template. In accordance with a preferred embodiment, and considering the triangular shape of the cranial hole, burr holes are formed at the respective ends of the template, and the remainder of the skull is cut away along the lines as defined by the template. As with the prior embodiment, it is appreciated the cranial hole may be made using any method acceptable to those skilled in the art. Given the matching shape of the cranial hole and the shunt plug 710, the shunt plug 710 will fit snugly within the cranial hole thereby minimizing potential movement after completion of the procedure.

With the cranial hole completed, the ventricular catheter 714 is positioned within the ventricle and the peritoneal catheter 716 is positioned within the body using well know medical procedures. Thereafter, the shunt plug housing 718 is positioned within the cranial hole with the upper surface 732 facing upwardly, and the ventricular catheter 714 is cut to an appropriate length. The ends of the peritoneal catheter 716 and the ventricular catheter 714 adjacent the shunt plug 710 are then secured to the shunt valve 712 and the shunt valve 712 is positioned within the shunt plug housing 718. In particular, the shunt plug 710 is mounted within the cranial hole 500 such that the upper surface 732 is substantially flush with the outer surface of the skull 520 and the projection 734*p* along the lower surface 734 is positioned within the cranial hole. As such, portions along the periphery of the shunt plug housing 718 overlie the skull, and screws may be passed therethrough to facilitate secure attachment of the shunt plug 710 to the skull. It is, however, appreciated the exact positioning of the shunt plug will vary based upon specific anatomical characteristics of the patient. Once the shunt plug 710 is properly positioned and secured in place using known techniques, the lucent disk 780 is positioned within the window recess 782.

In practice, and prior to initiating the surgical procedure, virtual images of the shunt plug 710, including both the shunt valve 712 and the lucent disk 780, are generated. Virtual images of the patient, including the approximate location of the shunt plug 710 are also generated. Upon initiation of the surgical procedure, movement of the actual shunt plug 710, including the shunt valve 712, shunt plug housing 718, and the lucent disk 780, relative to the patient is monitored in real-time. This is achieved by the integration of tracking devices (as discussed above with the prior embodiment shown with reference to FIG. 25) into or onto the respective shunt valve 712, shunt plug housing 718, and the lucent disk 780. Additional tracking devices may be applied to the patient in a manner known to those skilled in the art. It should be appreciated that the tracking devices may take a variety of forms so long as the computer-based guidance system is capable of identifying the real-time movement of the various components of the shunt plug 710 being tracked. For example, the tracking devices may take the form of external tracking devices attached to the shunt plug, tracking devices integrated into the shunt plug, or existing structures of the shunt plug that are readily identifiable via the sensing structure of the computer-based guidance system. Sensing may be achieved via various known techniques, including, but not limited to, infrared, electromagnetic, optical, etc. sensing techniques.

With this information and using a computer based surgical guidance system, the shunt plug 710 is properly positioned within the patient. Once the shunt valve 712 and the lucent disk 780 are properly positioned, they may be actuated utilizing well known procedures, and the procedure is completed in accordance with known medical procedures.

Considering the fact the lucent disk is optically transparent, optically translucent to all light waves, sonolucent, and/or radiolucent, various features have been integrated into the lucent disk in an effort to enhance the functionality thereof. While these features are described herein as individual embodiments, it is appreciated they may be combined in various combinations as the needs of a patient dictate.

Figure 30:
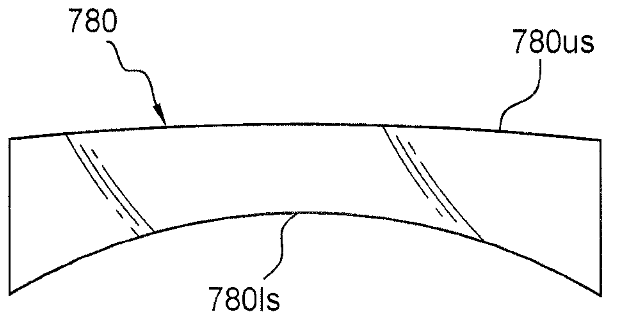
FIGS. 30, 31, and 32 are respectively a cross sectional view, a perspective view, and a cross sectional view showing various embodiments of a lucent disk.

In accordance with one embodiment as shown with reference to FIG. 30, the lucent disk 780' may be constructed with variations in shape designed to control the manner in which light, sound, radio, and other waves pass therethrough. Such variations in shape would be undertaken in a manner similar to the way in which eyeglasses are adjusted for each patient. For example, and with reference to the disclosed embodiment, the curvature of the upper surface 780*us* differs from the curvature of the lower surface 780*ls* wherein the upper surface 780*us* has a much larger radius of curvature.

Figure 31:
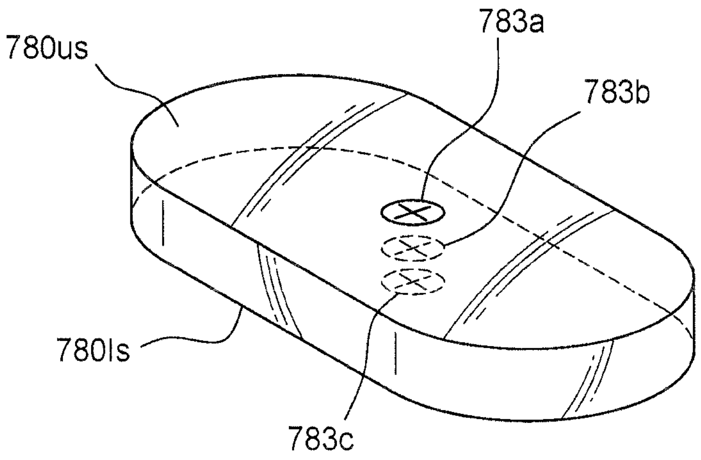

In accordance with another embodiment as shown with reference to FIG. 31, the lucent disk 780" may be constructed with an alignment feature 781. In accordance with a disclosed embodiment, the alignment feature 781 includes a series of markings 783*a-c* at different depths within the lucent disk. For example, an outer first lucent disk marking 783*a* and an inner second lucent disk marking 783*b* are formed along the upper and lower surfaces 780*us*, 780*ls*, respectively, of the lucent disk 780. One or more additional interior lucent disk markings 780*c* may be formed within the body of the lucent disk 780 and in alignment with the outer first lucent disk marking 783*a* and an inner second lucent disk marking 783*b*. While an outer first lucent disk marking 783*a*, an inner second lucent disk marking 783*b*, and at least one additional interior lucent disk marking 783*c* are disclosed herein, it is appreciated various combinations of markings may be used within the spirit of the present invention.

The outer first lucent disk marking 783*a*, the inner second lucent disk marking 783*b*, and the plurality of additional interior lucent disk markings 783*c* are aligned such that when a transmitter of light, sound, radio, or other waves is properly aligned with the markings, the light, sound, radio, or other waves will be directed to the proper location within the cranium. Similarly, when one looks through the lucent disk 780 and the outer first lucent disk marking 783*a*, the inner second lucent disk marking 783*b*, and the at least one additional interior lucent disk markings 783*c* merge into a single location identifying image (for example, crosshairs or circles), a specific brain anatomy (or other structural element upon the surface of the brain) is identified by the single location identifying image. When the specific brain anatomy identified by the single location identifying image changes over time, the surgeon will know that something has shifted and will take appropriate action.

Figure 32:
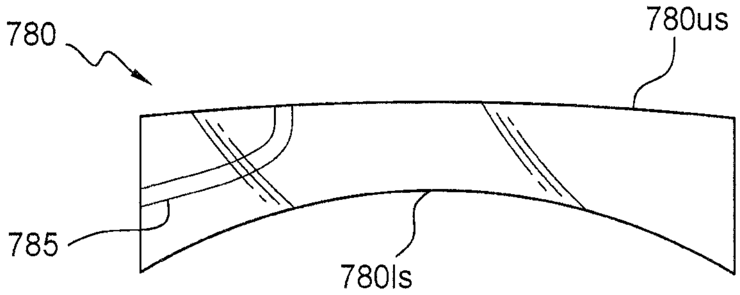

In accordance with one embodiment as shown with reference to FIG. 32, the lucent disk may be constructed with wire channels 785 oriented for various purposes specific to different patients and treatment protocols.

The use of a lucent disk offers various advantages to address specific needs within the industry. For example, patients requiring ventriculoperitoneal shunting are postoperatively left with a high-profile shunt valve underneath their scalp and have high rates of complication and revision due to infection, occlusion, extrusion, and/or migration (dislodging/disconnecting) of the valve. Additionally, monitoring of intracranial pressure and ventricular size can be difficult and costly when complications arise, requiring lumbar punctures and CT scans to diagnose effectively. Patients receiving and using the present lucent disk would benefit from reduced profile of the shunt valve (level with the skull), reducing complications associated with pressure on the valve and restoring the native contour of the cranium. As well, due to high level of complication involved with ventriculoperitoneal shunting, ultrasound diagnostics would prove beneficial to rapidly, and noninvasively, monitor the size of the ventricles to correlate efficacy of the shunt and potential necessity of revision.

Figure 33:
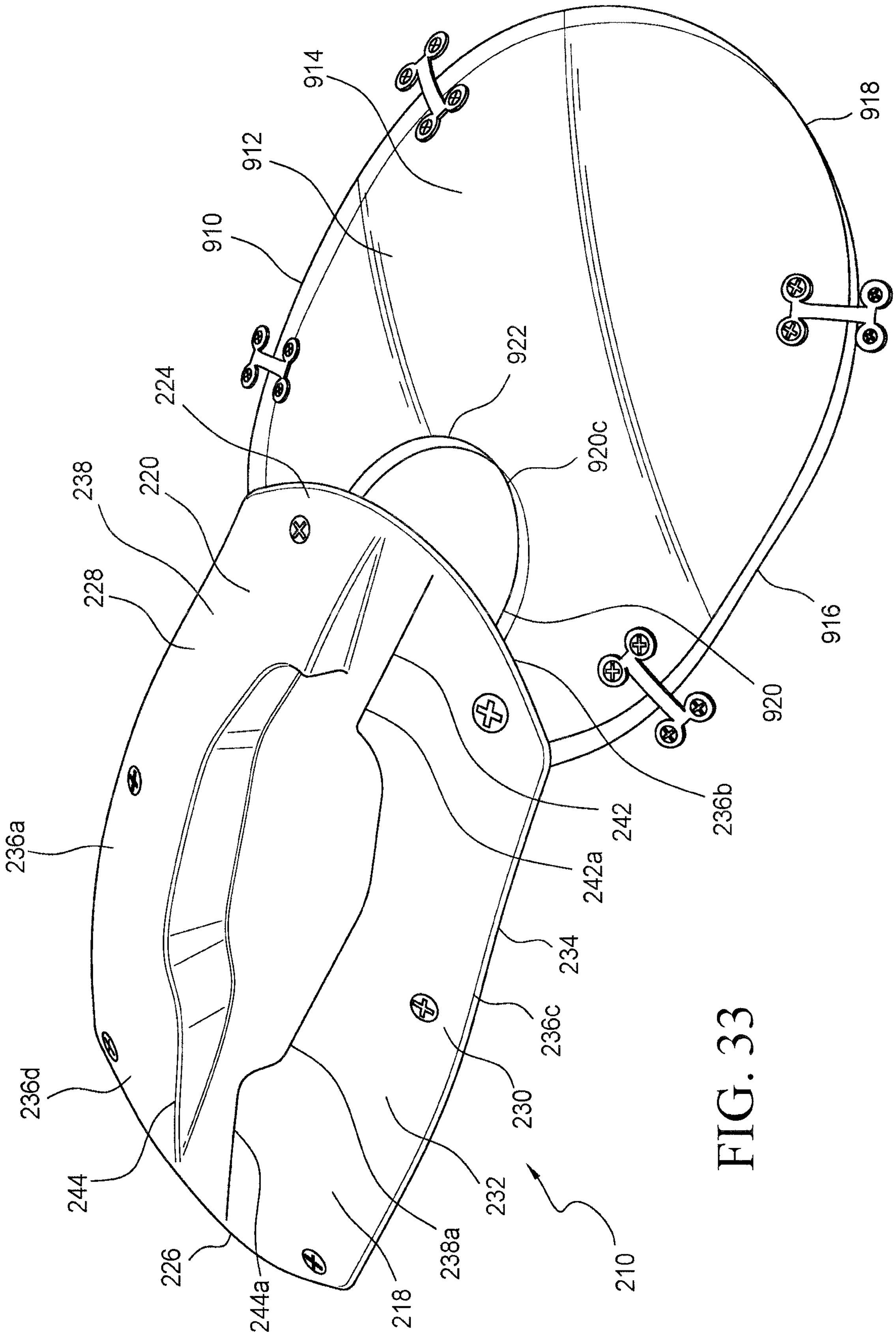
FIGS. 33, 34, and 35 are perspective views of a cerebral spinal fluid shunt plug assembly in accordance with alternate embodiments.
Figure 34:
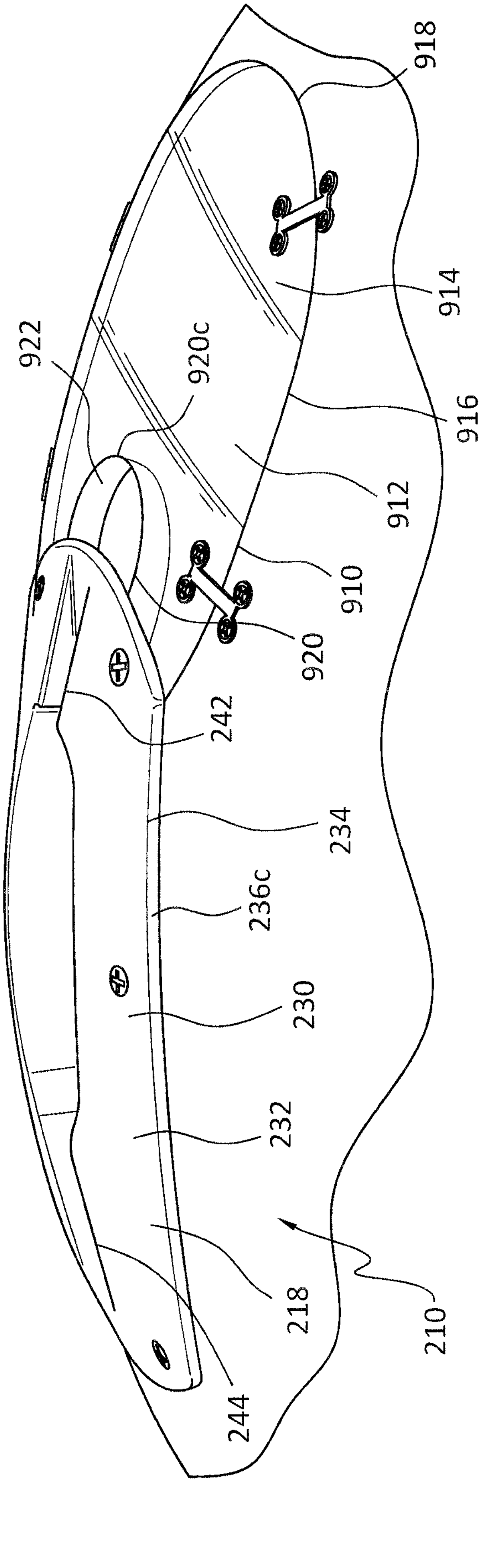
Figure 35:
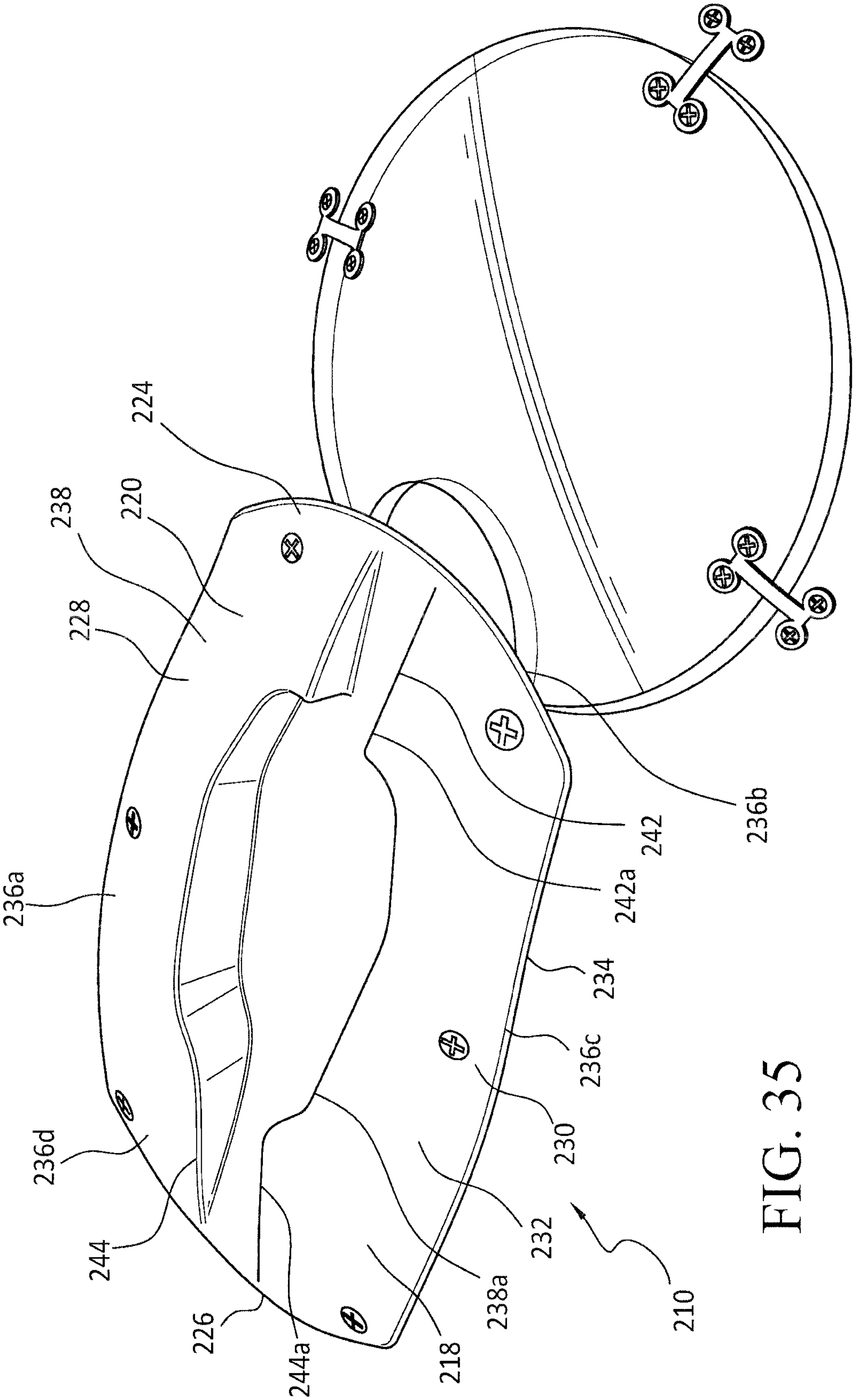

In accordance with yet another embodiment, the lucent element is integrated with the spinal fluid shunt plug 210 as a selectively attachable accessory in the form of a clear custom intercranial implant Referring to FIGS. 33 and 34, the spinal shunt plug is as described above with reference to FIGS. 9 to 18 and similar reference numerals will be used. The shunt plug 210 includes a shunt plug housing 218 composed of a bottom first housing member 220. The shunt plug housing 218 is substantially elliptically shaped (with curved and extended corners, as well as arcuate walls) and includes a first end 224, a second end 226, and first and second lateral sides 228, 230. However, and as with the prior embodiments, it is appreciated various shapes may be employed within the spirit of the present invention and the shape of the shunt plug housing may be varied without departing from the spirit of the present invention.

The shunt plug housing 218 also includes an upper surface 232, a lower surface 234, and continuous side walls 236*a-d* extending between the upper surface 232 and the lower surface 234, as well as about the periphery of the shunt plug housing 218. As will be appreciated based upon the following disclosure, and as with the embodiment of FIGS. 9-18, the lower surface 234 is provided with a projection (not shown) that ultimately fits within the cranial hole 1000 to assist in holding the shunt plug 210 in position after installation. With this in mind, the projection is shaped to fit within the cranial hole 500 as shown in FIG. 25.

A shunt valve recess 238 is formed within the upper surface 232 of the shunt plug housing 218. The shunt valve recess 238 is in communication with the exterior of the shunt plug housing 218 via access passageways 242, 244 extending from the exterior surface of the shunt plug housing 218 to the shunt valve recess 238. As will be explained below in greater detail, these access holes (or passageways) 242, 244 allow for connection of the ventricular catheter 214 and the peritoneal catheter 216 with the shunt valve 212 housed within the shunt valve recess 238 of the shunt plug housing 218. The access passageways 242, 244 are defined by recessed surfaces formed along the upper surface 232 of the shunt plug housing 218. Depending upon the shape of the shunt plug housing 218 and the shunt valve 212 to be positioned therein, the position of the access holes (or passageways) 242, 244 may be varied to optimize the ultimate positioning of the peritoneal catheter 216 and the ventricular catheter 214.

As discussed above, the shunt valve recess 238 in which the shunt valve 212 is positioned, as well as the access holes 242, 244 for the passage of the ventricular and peritoneal catheters 214, 216, are formed within the shunt plug housing 218. The shunt valve recess 238 and access holes 242, 244 are defined by recessed surfaces 238*a*, 242*a*, 244*a* formed along the upper surface 232 of the shunt plug housing 218. In particular, the recessed surface 238*a* defining the shunt valve recess 238 is formed along the upper surface 232 of the shunt plug housing 218; the recessed surface 242*a* defining the first access hole (or passageway) 242 is formed along the upper surface 232 adjacent the first end 224; and the recessed surfaces 244*a* defining the second access hole (or passageway) 244 are formed along the side wall 264*a* of the shunt plug housing 218 at the second end 226 thereof.

As briefly discussed above, the shunt valve recess 238 defined within the shunt plug housing 218 is shaped and dimensioned for placement of the shunt valve 212 therein. As those skilled in the art will appreciate, and as explained above in conjunction with the prior embodiment, a variety of shunt valves are known in the art and the present shunt plug housing 218 may be adapted to accommodate a variety of these shunt valves.

As will be explained below in detail, once the shunt valve 212 is positioned within the shunt valve recess 238 of the shunt plug housing 218 the shunt plug 210 of the present invention may be utilized for the purpose of performing a cerebral spinal fluid shunt procedure.

The lucent element of this embodiment is a clear custom intercranial implant 910 shaped and dimensioned for positioning adjacent to the shunt plug 210. The clear custom intercranial implant 910 includes an implant body 912 structured in a manner as used and known by those skilled in the art of cranial surgical procedures. The implant body 912 may take a variety of forms and is most commonly shaped and dimensioned for integration into the structure of a patient's skull; that is, the implant body has a geometry that substantially conforms to a resected portion of the patient's anatomy to which the implant is to be secured. Briefly, the implant body 912 includes an outer (commonly convex) first surface 914, an inner (commonly concave) second surface 916, and a peripheral edge 918 extending between the outer first surface 914 and the inner second surface 916. The implant body 912 is shaped and dimensioned for engagement with the skull of the patient upon implantation in a manner well known to those skilled in the field of neurosurgical and neuroplastic reconstructive procedures. The outer first surface 914 and inner second surface 916 of the implant body 912 are preferably curved in a superior to inferior direction, a posterior to anterior direction, and a medial to lateral direction. In addition, the peripheral edge 918 has a substantial taper for resting upon a matching taper formed along the skull. It is, however, appreciated that this taper may vary (or not exist at all, that is, the peripheral edge may be substantially perpendicular relative to the outer first surface and the inner second surface) depending upon the specific needs.

In accordance with an embodiment, the implant body 912 is fabricated from a wide array of commonly-available biomaterials including, but not limited to, clear PMMA (Poly(methyl methacrylate)), PEEK (Polyether ether ketone), PEKK (Polyetherketoneketone), porous polyethylene, flexible silicone, cubic zirconium, titanium alloy, allograft, autograft, xenograft, glass, and/or various other tissue-engineered constructs. In fact, some of the biomaterials used in this novel device may be resorbable versus permanent with respect to time. In accordance with one embodiment, the implant body is ideally made of clear PMMA since it's fully translucent to light, sonolucent to ultrasound such that it allows for the passage of ultrasonic waves without the production of echoes that are due to reflection (as first described by Gordon et al. in "Sonolucent Cranial Implants: Cadaveric study and Clinical Findings Supporting Diagnostic and Therapeutic Trans-Cranioplasty Ultrasound. J Craniofac Sing 2019 and Gordon et al. in "Trans-Cranioplasty Ultrasound (TCU) through a Sonolucent Cranial Implant Made of Poly-methyl methacrylate (PMMA): Phantom Study Comparing Ultrasound, CT and MRI. J Craniofac Surg 2019), permeable to low-coherence light used in optical coherence tomography (OCT), radiolucent such that it is permeable to various forms of electromagnetic radiation (for example, is permeable to ECoG (electrocorticographic) signals), and transparent for ideal visualization necessary for brain lead placement, catheter positioning, etc. This allows for the critical transmission of vital imaging with minimal distortion, such as direct visual inspection of the brain, ultrasound waves for brain pathology detection, low-coherence light used in optical coherence tomography (OCT), and wireless signal communication (i.e., electroencephalography or ECoG), which is essential for various neuromodulation devices. Another clear material that may be readily used in accordance with the present reconstructive cranial implant is cubic zirconium or plastic.

The optical clarity of the implant body 912 is important in that it provides for the provision of high optical clarity allowing for optical links connecting the external environment to the surface of the brain (for example, transmitting between the cortex and the other side of the reconstructive cranial implant). Visualization devices such as high-definition cameras, ultrasound probes, or optical coherence tomography (OCT) imaging devices may therefore be used in conjunction with the reconstructive cranial implant.

Still further, the implant body is constructed of a material allowing for imaging of the brain through the reconstructive cranial implant, for example, via ultra-sound or optical coherence tomography. It is known that clear PMMA will provide the ability to permit ultra-sound imaging of the brain therethrough so long as it is manufactured without additives that might function to block the radio waves of the imaging device.

While the majority of the peripheral edge 918 of the implant body defines a generally continuously curved surface shaped and dimensioned to sit within the resected portion of the skull, a mating segment 920 of the peripheral edge 918 of the implant body 912 is shaped and dimensioned for a mating coupling with the shunt plug housing 218.

In particular, and considering the curved shape of the shunt plug housing 218 at the first end 242 thereof, the mating segment 920 is formed with a relatively concave profile shaped and dimensioned to mate with the first end 242 of the shunt plug housing 218. At a central portion **920*c* of the mating segment, a further concave cut-out 922 is formed. The concave cut-out 922 is positioned for alignment with the first access passageways 242 and provides an opening for the ventricular catheter 214** for positioning a described above.

In practice, installation would be accomplished in a manner similar to the embodiments discussed above.

As with the embodiment disclosed above, various features may be integrated into the clear custom cranial implant in an effort to enhance the functionality thereof. While these features are described herein as individual embodiments, it is appreciated they may be combined in various combinations as the needs of a patient dictate.

While, the shunt plug housing and implant body of the various embodiments disclosed above are made of various materials as discussed above, it is contemplated, the shunt plug housing and/or implant body implant body could be of a multi-material construction with the use of different materials in different elements of the shunt plug housing and/or implant body so as to expand the functionality thereof.

Figure 36:
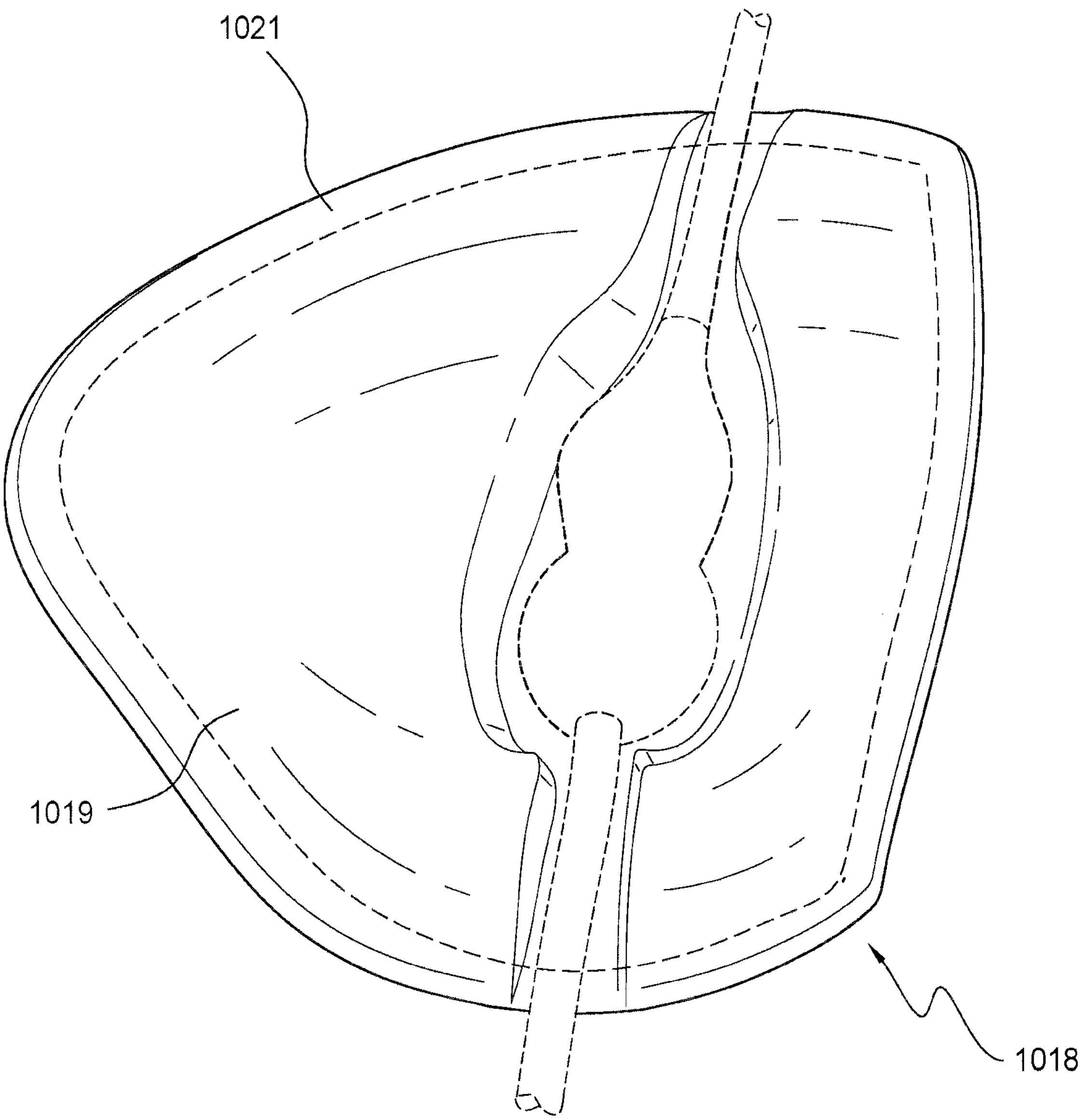
FIGS. 36, 37, and 38 are perspective views of a cerebral spinal fluid shunt plug assembly in accordance with further embodiments.
Figure 37:
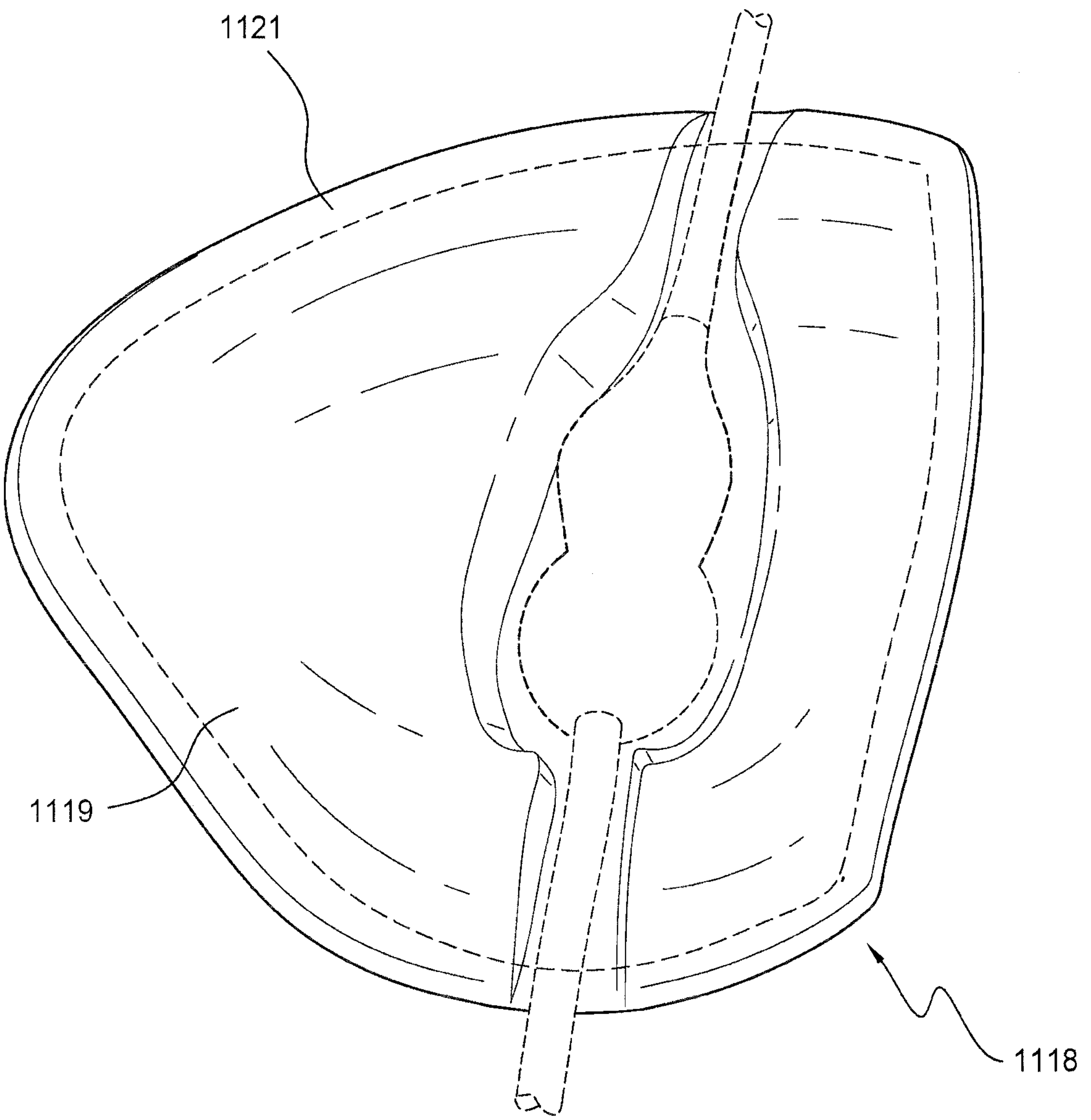
Figure 38:
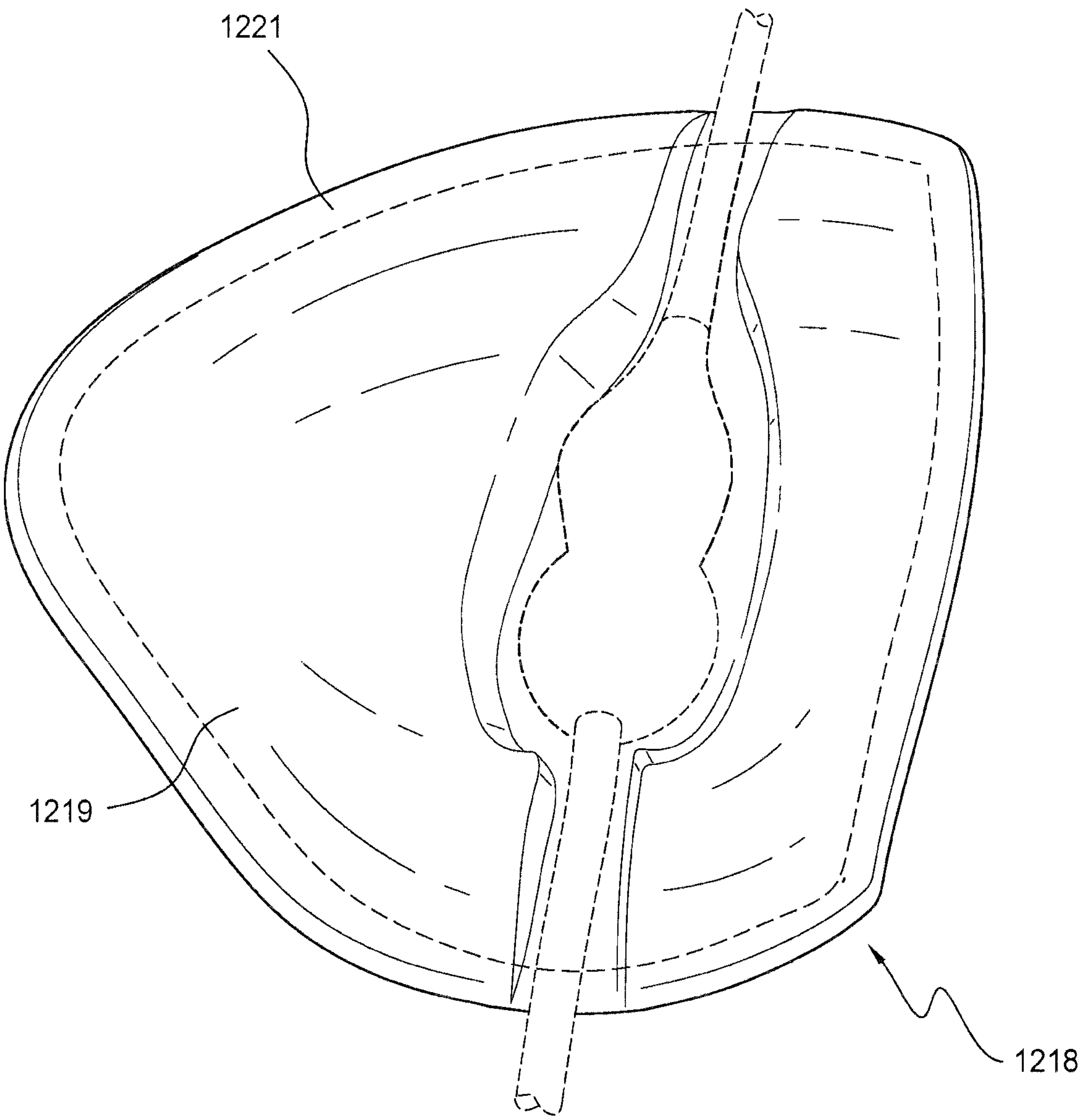

For example, and with reference to FIGS. 36 to 38, the shunt plug housing 1018 shown in FIG. 36 includes a central body member 1019 made of rigid sonolucent PMMA and a flexible perimeter member 1021 made of porous polyethylene. Such a construction provides medical practitioners with a large sonolucent area for transcranioplasty ultrasound as provided by the central body member 1019 and a malleable perimeter as provided by the perimeter member 1021 that optimizes a smooth transition between the implant perimeter and the native skull.

In accordance with another embodiment as shown with reference to FIG. 37, the shunt plug housing 1118 includes a central body member 1119 made of cubic zirconium (or any other rigid sonolucent material) and a flexible perimeter member 1021 made of expanded polytetrafluoroethylene (EPTFE), silicon, or other malleable material.

In accordance with yet another embodiment as shown in FIG. 38, the shunt plug housing 1218 could be a different composition of the same material, with the different compositions being selected to enhance sonolucency and aesthetic fixation. For example, the central body member 1219 of the shunt plug housing 1218 could be rigid sonolucent PMMA while the flexible perimeter member 1221 of the shunt plug housing 1218 could be PMMA with elastomer additives that change the material properties of the shunt plug housing from rigid to malleable. In this way, the implant could have an optimal smooth transition from the perimeter of the implant to the native skull.

While the embodiments presented above discuss the multi-material possibilities with regard to shunt plug housings only used with a shunt valve, such multi-material constructions could also be applied to the construction of implant bodies as disclosed with the other embodiments disclosed herein.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A cranial implant, comprising:

a housing including a first recess and a second recess formed therein;

the first recess is defined by recessed surfaces formed along surfaces of the housing, the first recess is in communication with an exterior surface of the housing via access passageways extending from the exterior surface of the housing to the first recess; and the second recess is formed within an upper surface of the housing and is provided with an access hole extending from the second recess to a lower surface of the housing, wherein the second recess is shaped and dimensioned to receive a head of a wireless intracranial monitoring device and the access hole is shaped and dimensioned for passage of a probe of a wireless intracranial monitoring device therethrough and to a desired position within the brain.

2. The cranial implant according to claim 1, further including an intracranial monitoring device shaped and dimensioned for passage through the access hole of the second recess.

3. The cranial implant according to claim 2, wherein the intracranial monitoring device is a wireless intracranial monitoring device.

4. The cranial implant according to claim 2, wherein the intracranial monitoring device includes a probe that passes through the access hole.

5. The cranial implant according to claim 1, wherein the access passageways are defined by recessed surfaces formed along the housing.

6. A cranial implant, comprising:

a housing including a first recess and a second recess formed therein, the housing also including an upper surface and a lower surface;

the first recess is defined by recessed surfaces formed along the housing, the first recess is in communication with an exterior surface of the housing via access passageways extending from the exterior surface of the housing to the first recess; and the second recess is formed within the upper surface of the housing and is provided with an access hole extending from the second recess to the lower surface of the housing, wherein the second recess is shaped and dimensioned to receive an intracranial monitoring device including a probe, wherein the second recess is separate and distinct from the first recess.

7. The cranial implant according to claim 6, further including an intracranial monitoring device shaped and dimensioned for passage through the access hole of the second recess.

8. The cranial implant according to claim 7, wherein the intracranial monitoring device is a wireless intracranial monitoring device.

9. The cranial implant according to claim 7, wherein the intracranial monitoring device includes a probe that passes through the access hole.

10. The cranial implant according to claim 6, wherein the access passageways are defined by recessed surfaces formed along the housing.

* * * * *